US008653101B2

(12) United States Patent
Kühnert et al.

(10) Patent No.: US 8,653,101 B2
(45) Date of Patent: Feb. 18, 2014

(54) SUBSTITUTED 2-OXY-QUINOLINE-3-CARBOXAMIDES AS KCNQ2/3 MODULATORS

(75) Inventors: Sven Kühnert, Düren (DE); Gregor Bahrenberg, Monschau-Konzen (DE); Achim Kless, Aachen (DE); Wolfgang Schröder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/218,512

(22) Filed: Aug. 26, 2011

(65) Prior Publication Data
US 2012/0053205 A1  Mar. 1, 2012

Related U.S. Application Data

(60) Provisional application No. 61/377,510, filed on Aug. 27, 2010.

(30) Foreign Application Priority Data

Aug. 27, 2010  (EP) ..................................... 10008921

(51) Int. Cl.
*A61K 31/04* (2006.01)
*C07D 215/38* (2006.01)

(52) U.S. Cl.
USPC ........................................... 514/312; 546/159

(58) Field of Classification Search
USPC ........................................... 514/312; 546/159
See application file for complete search history.

(56) References Cited

U.S. PATENT DOCUMENTS

| | | | |
|---|---|---|---|
| 4,181,658 A | 1/1980 | Hitzel et al. |
| 4,450,167 A | 5/1984 | Le Martret et al. |
| 4,500,348 A | 2/1985 | Hausmann et al. |
| 4,518,775 A | 5/1985 | Allais et al. |
| 4,542,127 A | 9/1985 | Hitzel et al. |
| 5,641,778 A | 6/1997 | Maibaum et al. |
| 5,646,150 A | 7/1997 | Behforouz et al. |
| 5,646,685 A | 7/1997 | Enokida |
| 5,719,157 A | 2/1998 | Sohda et al. |
| 6,030,983 A | 2/2000 | Behforouz et al. |
| 6,194,493 B1 | 2/2001 | Stahrfeldt et al. |
| 6,395,750 B1 | 5/2002 | Hedlund et al. |
| 6,555,685 B1 | 4/2003 | Freer et al. |
| 7,625,900 B2 | 12/2009 | Merla et al. |
| 7,696,238 B2 | 4/2010 | Merla et al. |
| 7,812,170 B2 | 10/2010 | Hughes et al. |
| 7,879,858 B2 | 2/2011 | Merla et al. |
| 8,017,772 B2 | 9/2011 | Merla et al. |
| 8,399,673 B2 | 3/2013 | Kühnert et al. |
| 8,445,512 B2 | 5/2013 | Kühnert et al. |
| 8,470,852 B2 | 6/2013 | Kuehnert et al. |
| 8,470,853 B2 | 6/2013 | Anderson et al. |
| 2002/0128277 A1 | 9/2002 | Dworetzky et al. |
| 2007/0249605 A1 | 10/2007 | Allen et al. |
| 2007/0254862 A1 | 11/2007 | Antel et al. |
| 2008/0167315 A1 | 7/2008 | Merla et al. |
| 2008/0221161 A1 | 9/2008 | Pinkerton et al. |
| 2009/0163545 A1 | 6/2009 | Goldfarb |
| 2009/0170840 A1 | 7/2009 | Roth et al. |
| 2009/0258880 A1 | 10/2009 | Merla et al. |
| 2009/0325948 A1 | 12/2009 | Hurley et al. |
| 2010/0004252 A1 | 1/2010 | Merla et al. |
| 2010/0105722 A1 | 4/2010 | Kuehnert et al. |
| 2010/0152234 A1 | 6/2010 | Kühnert et al. |
| 2010/0234372 A1 | 9/2010 | Kühnert et al. |
| 2010/0234419 A1 | 9/2010 | Kühnert et al. |
| 2010/0234421 A1 | 9/2010 | Kühnert et al. |
| 2010/0234428 A1 | 9/2010 | Kühnert et al. |
| 2010/0234429 A1 | 9/2010 | Kühnert et al. |
| 2011/0301208 A1 | 12/2011 | Padmanabhan et al. |
| 2012/0252841 A1 | 10/2012 | Kühnert et al. |

FOREIGN PATENT DOCUMENTS

| | | | |
|---|---|---|---|
| DE | 25 13 949 A1 | 10/1976 |
| DE | 2706977 A1 | 8/1978 |
| DE | 3111934 A1 | 10/1982 |
| DE | 3210063 A1 * | 9/1983 |
| DE | 32 11 934 A1 | 10/1983 |
| DE | 3211934 A1 | 10/1983 |
| EP | 0 089 597 | 9/1983 |
| EP | 0480258 A1 | 9/1991 |
| EP | 634169 A1 | 1/1995 |
| EP | 0716077 A1 | 6/1996 |
| EP | 0900824 A1 | 3/1999 |
| EP | 1142877 A1 | 10/2001 |
| EP | 1449841 A1 | 8/2004 |
| EP | 1 604 983 A1 | 12/2005 |
| FR | 2 532 939 | 3/1984 |
| GB | 1 495 124 | 12/1997 |

(Continued)

OTHER PUBLICATIONS

T.J. Coderre et al., Contribution of Central Neuroplasticity to Pathological Pain: Review of Clinical and Experimental Evidence, Elsevier Science Publishers, 1993, 52, 259-285.

Litchfield, J.T., Wilcoxon, J.J., A Simplified Method of Evaluating Dose-Effect Experiments, Stanford Research Laboratories, 1949, J. Pharmacol. Exp. Ther. 96, 99-113.

Ukrainets et al., 4-Hydroxy-2-Quinolones: Synthesis and Biological Properties of 2-Hydroxy-4-Imino-1,4-Dihydroquinoline-3-Carboxylic Acid N-R-Amides, Springer Science Business Media Inc., Chemistry of Heterocyclic Compounds, Kluwer, vol. 42, No. 4, 2006, pp. 475-487.

Ukrainets et al., 4-Hydroxy-2-Quinolones, Simple Synthesis of 1-Substituted 4-Methyl-2-Oxo-1,2-Dihydroquinoline-3Carboxylic Acids, Springer Science Business Media Inc., Chemistry of Heterocyclic Compounds, Kluwer, vol. 43, No. 1, 2007, pp. 58-62.

(Continued)

*Primary Examiner* — D M Seaman
(74) *Attorney, Agent, or Firm* — Norris McLaughlin & Marcus, P.A.

(57) ABSTRACT

The invention relates to substituted 2-oxy-quinoline-3-carboxamides, to pharmaceutical compositions containing these compounds and also to these compounds for use in the treatment and/or prophylaxis of pain and further diseases and/or disorders.

16 Claims, No Drawings

(56) References Cited

FOREIGN PATENT DOCUMENTS

| WO | 9626925 A1 | 9/1996 |
|---|---|---|
| WO | 0042026 A1 | 7/2000 |
| WO | 0110380 A2 | 2/2001 |
| WO | 0110381 A2 | 2/2001 |
| WO | 02066036 A1 | 8/2002 |
| WO | 02074388 A1 | 9/2002 |
| WO | 02081728 A2 | 10/2002 |
| WO | 2004026816 A1 | 4/2004 |
| WO | 2004026819 A2 | 4/2004 |
| WO | 2004058704 A2 | 7/2004 |
| WO | 2005035514 A2 | 4/2005 |
| WO | 2005049608 A1 | 6/2005 |
| WO | 2005105733 A1 | 11/2005 |
| WO | 2006051311 A1 | 5/2006 |
| WO | 2006092143 A1 | 9/2006 |
| WO | 2006122799 A1 | 11/2006 |
| WO | 2006122800 A1 | 11/2006 |
| WO | 2007015767 A1 | 2/2007 |
| WO | 2007030582 A2 | 3/2007 |
| WO | 2007057447 A1 | 5/2007 |
| WO | 2007070359 A2 | 6/2007 |
| WO | 2007070359 A3 | 6/2007 |
| WO | 2007133637 A1 | 11/2007 |
| WO | 2008/007211 | 1/2008 |
| WO | 2008011080 A2 | 1/2008 |
| WO | 2008011110 A2 | 1/2008 |
| WO | 2008012532 A2 | 1/2008 |
| WO | 2008/046582 | 4/2008 |
| WO | 2008/050199 | 5/2008 |
| WO | 2008/097976 | 8/2008 |
| WO | 2008113006 A2 | 9/2008 |
| WO | 2008121850 A2 | 10/2008 |
| WO | 2008127274 A2 | 10/2008 |
| WO | 2009018466 A1 | 2/2009 |
| WO | 2009019149 A1 | 2/2009 |
| WO | 2009052078 A1 | 4/2009 |
| WO | 2010/046108 | 4/2010 |
| WO | 2010039534 A2 | 4/2010 |
| WO | 2010039534 A3 | 4/2010 |
| WO | 2010075973 A1 | 7/2010 |
| WO | 2010/094644 | 8/2010 |
| WO | 2010/094645 | 8/2010 |

OTHER PUBLICATIONS

Ukrainets et al., 4-Hydroxy-2-Quinolones, Hydrochlorides of Amides of 1-Allyl-4-Hydroxy-6,7-Dimethoxy-2- Oxo-1,2Dihydro-Quinoline-3-Carboxylic Acid—A new Class of Opiod Receptor Antagonists, Springer Science Business Media Inc., Chemistry of Heterocyclic Compounds, Kluwer, vol. 46, No. 4, 2010, pp. 445-451.
Ravin, Louis. Preformulation. Chapter 76. In Remington's Pharmaceutical Sciences, 17th Ed, 1985.
Disanto, Anthony. Bioavailability and Bioequivalency Testing. Chapter 77. In Remington's Pharmaceutical Sciences, 17th Ed, 1985.
Knevel, Adelbert. Separation. Chapter 78. In Remington's Pharmaceutical Sciences, 17th Ed, 1985.
Phillips, G. Briggs. Sterilization. Chapter 79. In Remington's Pharmaceutical Sciences, 17th Ed, 1985.
Siegel, Frederick. Tonicity, Osmoticity, Osmolality, and Osmolarity. Chapter 80. In Remington's Pharmaceutical Sciences, 17th Ed, 1985.
Giles et al. Plastic Packaging Materials. Chapter 81. In Remington's Pharmaceutical Sciences, 17th Ed, 1985.
Lintner, Carl. Stability of Pharmaceutical Products. Chapter 82. In Remington's Pharmaceutical Sciences, 17th Ed, 1985.
Erskine, Jr., Clyde. Quality Assurance and Control. Chapter 83. In Remington's Pharmaceutical Sciences, 17th Ed, 1985.
Nairn, J.G., Solutions, Emulsion, Suspensions and Extractives. Chapter 84. In Remington's Pharmaceutical Sciences, 17th Ed, 1985.
Avis, Kenneth. Parenteral Preparations. Chapter 85. In Remington's Pharmaceutical Sciences, 17th Ed, 1985.
Turco et al. Intravenous Admixtures. Chapter 86. In Remington's Pharmaceutical Sciences, 17th Ed, 1985.

Mullins, John. Ophthalmic Preparations. Chapter 87.In Remington's Pharmaceutical Sciences, 17th Ed, 1985.
Block, Lawrence. Medicated Applications. Chapter 88. In Remington's Pharmaceutical Sciences, 17th Ed, 1985.
Rippie, Edward. Powders. Chapter 89. In Remington's Pharmaceutical Sciences, 17th Ed, 1985.
King et al. Oral Solid Dosage Forms. Chapter 90. In Remington's Pharmaceutical Sciences, 17th Ed, 1985.
Porter, Stuart. Coating of Pharmaceutical Dosage Forms. Chapter 91. In Remington's Pharmaceutical Sciences, 17th Ed, 1985.
Longer et al. Sustained-Release Drug Delivery Systems. Chapter 92. In Remington's Pharmaceutical Sciences, 17th Ed, 1985.
Sciarra et al. Aerosols. Chapter 93. In Remington's Pharmaceutical Sciences, 17th Ed, 1985.
Passmore et al., "KCNQ/M currents in sensory neurons: significance for pain therapy"; J. Neurosci. 2003; 23(18): 7227-36.
Blackburn-Munro and Jensen, "The anticonvulsant retigabine attenuates nociceptive behaviours in rat models of persistent and neuropathic pain"; Eur J Pharmacol. 2003; 460(2-3); 109-116.
Dost et al., "The anit-hyperalgesic activity of retigabine is mediated by KCNQ potassium channel activation" Naunyn Schmiedebergs Arch Pharmacol 2004; 369(4): 382-390.
Nielsen et al., "Pharmacological characterisation of acid-induced muscle allodynia in rats" Eur J Pharmacol. 2004; 487 (1-3): 93-103.
Gribkoff, "The therapeutic potential of neuronal KCNQ channel modulators" Expert Opin Ther Targets 2003; 7(6): 737-748.
Korsgaard et al., "Anxiolytic effects of maxipost (BMS-204352) and retigabine via activation of neuronal Kv7 channels"; J Pharmacol Exp Ther. 2005, 14(1): 282-92.
Wickenden et al., "KCNQ potassium channels: drug targets for the treatment of epilepsy and pain"; Expert Opin Ther Pat 2004; 14(4): 457-469.
Gribkoff, "The therapeutic potential of neuronal Kv7 (KCNQ) channel modulators: an update", Expert Opin Ther Targets 2008, 12(5): 565-81.
Miceli et al., "Molecular pharmacology and therapeutic potential of neuronal Kv7-modulating drugs"; Curr Opin Pharmacol 2008, 8(1): 65-74.
Streng et al., "Urodynamic effects of the K+ channel (KCNQ) opener retigabine in freely moving, conscious rats"; J Urol 2004; 172: 2054-2058.
Hansen et al., "The neuronal KCNQ channel opener retigabine inhibits locomotor activity and reduces forebrain excitatory responses to the psychostimulants cocaine, methylphenidate and phencyclidine"; Eur J Pharmacol 2007, 570(1-3): 77-88.
Dencker et al., "Effect of the new antiepileptic drug retigabine in a rodent model of mania"; Epilepsy Behav 2008, 12 (1): 49-53.
Richter et al., "Antidystonic effects of Kv7 (KCNQ) channel openers in the dtsz mutant, an animal model of primary paroxysmal dystonia"; Br J Pharmacol 2006, 149(6): 747-53.
Remington's Pharmaceutical Sciences, A.R. Gennaro (Editor), 17th edition, Mack Publishing Company, Easton, Pa, 1985, Part 8, Chapters 76 to 93.
Bennett, G.J. and Xie, Y.K., A peripheral mononeuropathy in rat that produces disorders of pain sensation like those seen in man, Pain 1988, 33(1), 87-107.
Kim, S.H. and Chung, J.M., An experimental model for peripheral neuropathy produced by segmental spinal nerve ligation in the rat, Pain 1992, 50(3), 355-363.
D'Amour and Smith, "A method for determining loss of pain sensation"; J. Pharm. Exp. Ther. 72, 74 79 (1941).
D. Dubuisson et al., "The formalin test: a quantitative study of the analgesic effects of morphine, meperidine, and brain stem stimulation in rats and cats"; Pain 1977, 4, 161-174.
De Sarro et al., Naunyn-Schmiedeberg's Arch. Pharmacol. 2001, 363, 330-336.
T.J. Coderre et al., Pain 1993, 52, pp. 259-285.
CAPLUS 1972:59403.
F. A. Carey, R.J. Sundberg, Advanced Organic Chemistry, Parts A and B, Springer, 5th edition, 2007.

(56) References Cited

OTHER PUBLICATIONS

Hewawasam et al., The synthesis and structure activity relationship of 3-amino-4-benzylquinolin-2-ones: discovery of novel KCNQ2 channel openers; 14 Bioorg & Med. Chem. Letters, pp. 1615-1618 (2004).

J. March, Advanced Organic Chemistry, Wiley & Sons, 6th edition, 2007.

Martin, Yvonne et al., "Do structurally similar molecules have similar biological activity?"; 45 J. Med. Chem. pp. 4350-4358, 4536 (2002).

Patani, G. et al., Bioisosterism: a rational approach in drug design, Chem Rev. 1996, pp. 3146-3176.

Silverman, R. The organic chemistry of drug design and drug action, 2004, Elsevier, 2nd edition, pp. 9.

Wermuth, Camille G. "Molecular Variations Based on Isoteric Replacements", The Practice of Medicinal Chemistry, (1996) pp. 203-237.

Yoo et al., "Beckmann rearrangement using indium (III)chloride: synthesis of substituted oxazoloquinolines from the corresponding ketoximes of 3-acyl-1H-quinolin-4-ones"; Synthesis (2006), No. 10, pp. 1599-1612.

F. Zaragoza Dorwald; "Side reactions in organic synthesis; a guide to successful synthesis design", Wiley-VCH, Winheim, preface, pp. ix (2005).

PCT Search Report for International application No. PCT/EP2011/004277, mailed on Oct. 10, 2011.

PCT Search Report for International application No. PCT/EP2011/004278, mailed on Oct. 11, 2011.

PCT Search Report for International application No. PCT/EP2011/004279, mailed on Oct. 11, 2011.

PCT Search Report for International application No. PCT/EP2011/004280, mailed on Oct. 11, 2011.

PCT Search Report for International application No. PCT/EP2011/004369, mailed on Jan. 30, 2012.

Ukrainets et al., Chemistry of Heterocyclic Compounds, vol. 45, 2009.

Vittorio, F. et al; "Ricerche su derivati alchilici della isochinolina" Farmaco, Edizione Scientificia (1984) 39(3), pp. 229-245 (English Abstract provided).

McKinnell, et al; "A multivalent approach to the design and discovery of orally efficacious 5-HT4 receptor agonists"; J. Med. Chem. (2009), 52, pp. 5330-5343.

\* cited by examiner

SUBSTITUTED 2-OXY-QUINOLINE-3-CARBOXAMIDES AS KCNQ2/3 MODULATORS This application claims priority of European Patent Application No. 10 008 921.8, filed on Aug. 27, 2010, and U.S. Provisional Application No. 61/377,510, filed on Aug. 27, 2010, the entire contents of which are incorporated herein by reference.

The invention relates to substituted 2-oxy-quinoline-3-carboxamides, to pharmaceutical compositions containing these compounds and also to these compounds for use in the treatment and/or prophylaxis of pain and further diseases and/or disorders.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood the successful and satisfactory treatment of pain for the patient, is also documented in the large number of scientific works which have recently been published in the field of applied analgesics and of fundamental research into nociception.

A pathophysiological feature of chronic pain is the over-excitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36).

It has accordingly been possible to detect an analgesic activity in preclinical neuropathy and inflammatory pain models for the KCNQ2/3 agonist retigabine (Blackburn-Munro and Jensen, Eur J. Pharmacol. 2003; 460(2-3); 109-16; post et al., Naunyn Schmiedebergs Arch Pharmacol 2004; 369(4): 382-390).

The KCNQ2/3 $K^+$ channel thus represents a suitable starting point for the treatment of pain; in particular of pain selected from the group consisting of chronic pain, acute pain, neuropathic pain, inflammatory pain, visceral pain and muscular pain (Nielsen et al., Eur J. Pharmacol. 2004; 487(1-3): 93-103), in particular of neuropathic and inflammatory pain. Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53) and dystonia-associated dyskinesias (Richter et al., Br J Pharmacol 2006, 149(6): 747-53).

Substituted quinolines and other compounds are known from e.g. FR 2 532 939, WO 2010/094644, WO 2010/094645, WO 2008/007211, WO 2008/050199, and EP 0 089 597.

Substituted compounds that have an affinity for the KCNQ2/3 $K^+$ channel are e.g. known from the prior art (WO 2008/046582, WO 2010/046108). Substituted sulfonyl urea compounds are e.g. known from EP 0 089 597 A2. Heterocyclic modulators of TGR5 are e.g. known from WO 2008/097976 A1.

There is a demand for further compounds having comparable or better properties, not only with regard to affinity to KCNQ2/3 $K^+$ channels per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example. A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions, or no interactions at all, of pharmaceutical compositions are to be expected.

In addition, it may be advantageous if the compounds show a high selectivity towards other receptors of the KCNQ family (specificity), e.g. towards KCNQ1, KCNQ3/5 or KCNQ4. A high selectivity may have a positive effect on the side effects profile: for example it is known that compounds which (also) have an affinity to KCNQ1 are likely to have a potential for cardial side effects. Therefore, a high selectivity towards KCNQ1 may be desirable. However, it may also be advantageous for the compounds to show a high selectivity towards other receptors. For instance, it may be advantageous for the compounds to show a low affinity for the hERG ion channel or the L-type calcium ion channel (phenylalkylamine-, benzothiazepin-, dihydropyridine-binding site) since these receptors are known to possibly have a potential for cardial side effects. Further, an improved selectivity towards binding to other endogenic proteins (i.e. receptors or enzymes) may result in a better side effects profile and, consequently to an improved tolerance.

It was therefore an object of the invention to provide new compounds having advantages over the compounds of the prior art. These compounds should be suitable in particular as pharmacological active ingredients in pharmaceutical compositions, preferably in pharmaceutical compositions for the treatment and/or prophylaxis of disorders and/or diseases which are mediated, at least in part, by KCNQ2/3 $K^+$ channels.

That object is achieved by the subject-matter of the patent claims.

It has been found, surprisingly, that substituted compounds of the general formula (I) given below are suitable for the treatment of pain. It has also been found, surprisingly, that substituted compounds of the general formula (I) given below also have an excellent affinity for the KCNQ2/3 $K^+$ channel and are therefore suitable for the prophylaxis and/or treatment of disorders and/or diseases that are mediated at least in part by KCNQ2/3 $K^+$ channels. The substituted compounds thereby act as modulators, i.e. agonists or antagonists, of the KCNQ2/3 $K^+$ channel.

The present invention therefore relates to a substituted compound of general formula (I),

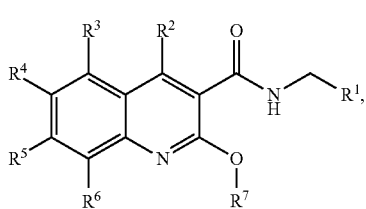 (I)

wherein

R¹ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

R² represents H; F; Cl; Br; I; CN; CF₃; C(=O)H; NO₂; OCF₃; SCF₃; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)₂, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)₂—$C_{1-4}$-aliphatic residue, a S(=O)₂—O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

R³, R⁴, R⁵ and R⁶ each independently of one another represent H; F; Cl; Br; I; CN; CF₃; C(=O)H; C(=O)—OH; C(=O)—NH₂; SCF₃; S(=O)₂—OH; NO₂; OCF₃; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)₂, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)₂—$C_{1-4}$-aliphatic residue, a S(=O)₂—O—$C_{1-4}$-aliphatic residue, wherein the $C_{1-4}$ aliphatic residue may be in each case be unsubstituted or mono- or polysubstituted; a NH($C_{1-4}$ aliphatic residue), a N($C_{1-4}$ aliphatic residue)₂, a NH—C(=O)—$C_{1-4}$ aliphatic residue, a NH—S(=O)₂—$C_{1-4}$-aliphatic residue, a N($C_{1-4}$ aliphatic residue)-C(=O)—$C_{1-4}$ aliphatic residue, or a N($C_{1-4}$ aliphatic residue)-S(=O)₂—$C_{1-4}$ aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

R⁷ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if R⁷ denotes a 3 to 10 membered heterocycloaliphatic residue, the 3 to 10 membered heterocycloaliphatic residue is linked via a carbon atom, in which an "aliphatic group" and "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, NO₂, NH₂, an NH($C_{1-4}$ aliphatic residue), an N($C_{1-4}$ aliphatic residue)₂, a NH—C(=O)—$C_{1-4}$ aliphatic residue, a NH—S(=O)₂—$C_{1-4}$ aliphatic residue, =O, OH, OCF₃, a O—$C_{1-4}$-aliphatic residue, a O—C(=O)—$C_{1-4}$-aliphatic residue, SH, SCF₃, a S—$C_{1-4}$-aliphatic residue, S(=O)₂OH, a S(=O)₂—$C_{1-4}$-aliphatic residue, a S(=O)₂—O—$C_{1-4}$-aliphatic residue, a S(=O)₂—NH—$C_{1-4}$-aliphatic residue, CN, CF₃, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—NH₂, a C(=O)—NH($C_{1-4}$ aliphatic residue), and a C(=O)—N($C_{1-4}$ aliphatic residue)₂;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, NO₂, NH₂, an NH($C_{1-4}$ aliphatic residue), an N($C_{1-4}$ aliphatic residue)₂, a NH—C(=O)—$C_{1-4}$ aliphatic residue, a NH—S(=O)₂—$C_{1-4}$ aliphatic residue, =O, OH, OCF₃, a O—$C_{1-4}$-aliphatic residue, a O—C(=O)—$C_{1-4}$-aliphatic residue, SH, SCF₃, a S—$C_{1-4}$-aliphatic residue, S(=O)₂OH, a S(=O)₂—$C_{1-4}$-aliphatic residue, a S(=O)₂—O—$C_{1-4}$-aliphatic residue, a S(=O)₂—NH—$C_{1-4}$-aliphatic residue, CN, CF₃, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—NH₂, a C(=O)—NH($C_{1-4}$ aliphatic residue), and a C(=O)—N($C_{1-4}$ aliphatic residue)₂;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO₂, NH₂,

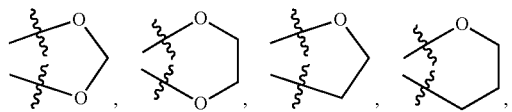

an NH($C_{1-4}$ aliphatic residue), an N($C_{1-4}$ aliphatic residue)₂, an NH—C(=O)—$C_{1-4}$ aliphatic residue, an NH—

S(=O)₂—C₁₋₄ aliphatic residue, OH, OCF₃, a O—C₁₋₄-aliphatic residue, a O—C(=O)—C₁₋₄-aliphatic residue, SH, SCF₃, a S—C₁₋₄ aliphatic residue, S(=O)₂OH, a S(=O)₂—C₁₋₄-aliphatic residue, a S(=O)₂—O—C₁₋₄-aliphatic residue, a S(=O)₂—NH—C₁₋₄-aliphatic residue, CN, CF₃, C(=O)H, C(=O)OH, a C₁₋₄-aliphatic residue, a C(=O)—C₁₋₄-aliphatic residue, a C(=O)—O—C₁₋₄-aliphatic residue, a C₃₋₈-cycloaliphatic residue, a 3 to 6 membered heterocycloaliphatic residue, benzyl, aryl, heteroaryl, C(=O)—NH₂, a C(=O)—NH(C₁₋₄ aliphatic residue), and a C(=O)—N(C₁₋₄ aliphatic residue)₂;

in the form of the free compounds, the racemate, the enantiomers, diastereomers, mixtures of the enantiomers or diastereomers in any mixing ratio, or of an individual enantiomer or diastereomer, or in the form of the salts of physiologically acceptable acids or bases, or in the form of the solvates, in particular hydrates.

The terms "C₁₋₁₀-aliphatic residue", "C₁₋₈-aliphatic residue", "C₁₋₈-aliphatic residue" and "C₁₋₄-aliphatic residue" and "C₁₋₂-aliphatic residue" comprise in the sense of this invention acyclic saturated or unsaturated aliphatic hydrocarbon residues, which can be branched or unbranched and also unsubstituted or mono- or polysubstituted, containing 1 to 10, or 1 to 8, or 1 to 6, or 1 to 4 or 1 to 2 carbon atoms, respectively, i.e. C₁₋₁₀ alkanyls, C₂₋₁₀ alkenyls and C₂₋₁₀ alkynyls as well as C₁₋₈ alkanyls, C₂₋₈ alkenyls and C₂₋₈ alkynyls as well as C₁₋₆ alkanyls, C₂₋₆ alkenyls and C₂₋₆ alkynyls as well as C₁₋₄ alkanyls, C₂₋₄ alkenyls and C₂₋₄ alkynyls, as well as C₁₋₂ alkanyls, C₂ alkenyls and C₂ alkynyls, respectively. In this case, alkenyls comprise at least one C—C double bond (a C=C-bond) and alkynyls comprise at least one C—C triple bond (a C≡C-bond). Preferably, aliphatic residues are selected from the group consisting of alkanyl (alkyl) and alkenyl residues, more preferably are alkanyl residues. Preferred C₁₋₁₀ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl and n-decyl. Preferred C₁₋₈ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl and n-octyl. Preferred C₁₋₆ alkanyl residues are selected from the group consisting of methyl, ethyl, n-propyl, 2-propyl, n-butyl, isobutyl, sec.-butyl, tert.-butyl, n-pentyl, isopentyl, neopentyl and n-hexyl. Preferred C₁₋₄ alkanyl residues are selected from the group consisting of methyl, ethyl, n-propyl, 2-propyl, n-butyl, isobutyl, sec.-butyl and tert.-butyl. Preferred C₂₋₁₀ alkenyl residues are selected from the group consisting of ethenyl (vinyl), propenyl (—CH₂CH=CH₂, —CH=CH—CH₃, —C(=CH₂)—CH₃), butenyl, pentenyl, hexenyl heptenyl, octenyl, nonenyl and decenyl. Preferred C₂₋₈ alkenyl residues are selected from the group consisting of ethenyl (vinyl), propenyl (—CH₂CH=CH₂, —CH=CH—CH₃, —C(=CH₂)—CH₃), butenyl, pentenyl, hexenyl heptenyl and octenyl. Preferred C₂₋₆ alkenyl residues are selected from the group consisting of ethenyl (vinyl), propenyl (—CH₂CH=CH₂, —CH=CH—CH₃, —C(=CH₂)—CH₃), butenyl, pentenyl and hexenyl. Preferred C₂₋₄ alkenyl residues are selected from the group consisting of ethenyl (vinyl), propenyl (—CH₂CH=CH₂, —CH=CH—CH₃, —C(=CH₂)—CH₃) and butenyl. Preferred C₂₋₁₀ alkynyl residues are selected from the group consisting of ethynyl, propynyl (—CH₂—C≡CH, —C≡C—CH₃), butynyl, pentynyl, hexynyl, heptynyl, octynyl, nonynyl and decynyl. Preferred C₂₋₈ alkynyl residues are selected from the group consisting of ethynyl, propynyl (—CH₂—C≡CH, —C≡C—CH₃), butynyl, pentynyl, hexynyl, heptynyl and octynyl. Preferred C₂₋₆ alkynyl residues are selected from the group consisting of ethynyl, propynyl (—CH₂—C≡CH, —C≡C—CH₃), butynyl, pentynyl and hexynyl. Preferred C₂₋₄ alkynyl residues are selected from the group consisting of ethynyl, propynyl (—CH₂—C≡CH, —C≡C—CH₃) and butynyl.

The terms "C₃₋₆ cycloaliphatic residue" and "C₃₋₁₀ cycloaliphatic residue" mean for the purposes of this invention cyclic aliphatic hydrocarbons containing 3, 4, 5 or 6 carbon atoms and 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloaliphatic residues can be bound to the respective superordinate general structure via any desired and possible ring member of the cycloaliphatic residue. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues which can in turn be unsubstituted or mono- or polysubstituted. C₃₋₁₀ cycloaliphatic residue can furthermore be singly or multiply bridged such as, for example, in the case of adamantyl, bicyclo[2.2.1]heptyl or bicyclo[2.2.2]octyl. Preferred C₃₋₁₀ cycloaliphatic residues are selected from the group consisting of cyclopropyl, cyclobutyl, cyclopentyl, cyclohexyl, cycloheptyl, cyclooctyl, cyclononyl, cyclodecyl, adamantyl,

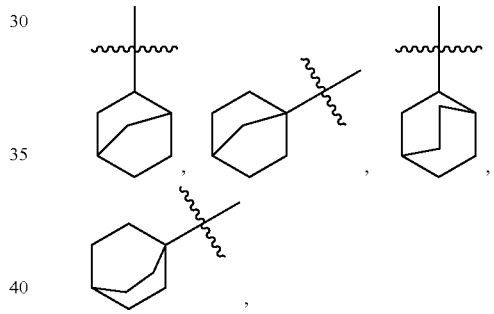

cyclopentenyl, cyclohexenyl, cycloheptenyl and cyclooctenyl. Preferred C₃₋₆ cycloaliphatic residues are selected from the group consisting of cyclopropyl, cyclobutyl, cyclopentyl, cyclohexyl, cyclopentenyl and cyclohexenyl.

The terms "3-6-membered heterocycloaliphatic residue" and "3-10-membered heterocycloaliphatic residue" mean for the purposes of this invention heterocycloaliphatic saturated or unsaturated (but not aromatic) residues having 3-6, i.e. 3, 4, 5 or 6 ring members, and 3-10, i.e. 3, 4, 5, 6, 7, 8, 9 or 10 ring members, respectively, in which in each case at least one, if appropriate also two or three carbon atoms are replaced by a heteroatom or a heteroatom group each selected independently of one another from the group consisting of O, S, S(=O)₂, N, NH and N(C₁₋₈ alkyl), preferably N(CH₃), wherein the ring members can be unsubstituted or mono- or polysubstituted. The heterocycloaliphatic residue can be bound to the superordinate general structure via any desired and possible ring member of the heterocycloaliphatic residue. The heterocycloaliphatic residues can also be condensed with further saturated, (partially) unsaturated (hetero)cycloaliphatic or aromatic or heteroaromatic ring systems, i.e. with cycloaliphatic, heterocycloaliphatic, aryl or heteroaryl residues, which can in turn be unsubstituted or mono- or polysubstituted. Preferred heterocycloaliphatic residues are selected from the group consisting of azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, 4-methylpiperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl.

The term "aryl" means for the purpose of this invention aromatic hydrocarbons having 6 to 14 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl, oxazolyl, thiazolyl and thienyl are particularly preferred.

The terms "aryl, heteroaryl, a heterocycloaliphatic residue, or a cycloaliphatic residue bridged via a $C_{1-4}$-aliphatic group or via a $C_{1-8}$-aliphatic group" mean for the purpose of the invention that the expressions "aryl, heteroaryl, heterocycloaliphatic residue and cycloaliphatic residue" have the above-defined meanings and are bound to the respective superordinate general structure via a $C_{1-4}$-aliphatic group or via a $C_{1-8}$-aliphatic group, respectively. The $C_{1-4}$ aliphatic group and the $C_{1-8}$-aliphatic group can in all cases be branched or unbranched, unsubstituted or mono- or polysubstituted. The $C_{1-4}$ aliphatic group can in all cases be furthermore saturated or unsaturated, i.e. can be a $C_{1-4}$ alkylene group, a $C_{2-4}$ alkenylene group or a $C_{2-4}$ alkynylene group. The same applies to a $C_{1-8}$-aliphatic group, i.e. a $C_{1-8}$-aliphatic group can in all cases be furthermore saturated or unsaturated, i.e. can be a $C_{1-8}$ alkylene group, a $C_{2-8}$ alkenylene group or a $C_{2-8}$ alkynylene group. Preferably, the $C_{1-4}$-aliphatic group is a $C_{1-4}$ alkylene group or a $C_{2-4}$ alkenylene group, more preferably a $C_{1-4}$ alkylene group. Preferably, the $C_{1-8}$-aliphatic group is a $C_{1-8}$ alkylene group or a $C_{2-8}$ alkenylene group, more preferably a $C_{1-8}$ alkylene group. Preferred $C_{1-4}$ alkylene groups are selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$— and —$C(CH_3)(CH_2CH_3)$—. Preferred $C_{2-4}$ alkenylene groups are selected from the group consisting of —$CH=CH$—, —$CH=CH$—$CH_2$—, —$C(CH_3)=CH_2$—, —$CH=CH$—$CH_2$—$CH_2$—, —$CH_2$—$CH=CH$—$CH_2$—, —$CH=CH$—$CH=CH$—, —$C(CH_3)=CH$—$CH_2$—, —$CH=C(CH_3)$—$CH_2$—, —$C(CH_3)=C(CH_3)$— and —$C(CH_2CH_3)=CH$—. Preferred $C_{2-4}$ alkynylene groups are selected from the group consisting of —$C\equiv C$—, —$C\equiv C$—$CH_2$—, —$C\equiv C$—$CH_2$—$CH_2$—, —$C\equiv C$—$CH(CH_3)$—, —$CH_2$—$C\equiv C$—$CH_2$— and —$C\equiv C$—$C\equiv C$—. Preferred $C_{1-8}$ alkylene groups are selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$—$CH$($CH_3$)—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—. Preferred $C_{2-8}$ alkenylene groups are selected from the group consisting of —$CH=CH$—, —$CH=CH$—$CH_2$—, —$C(CH_3)=CH_2$—, —$CH=CH$—$CH_2$—$CH_2$—, —$CH_2$—$CH=CH$—$CH_2$—, —$CH=CH$—$CH=CH$—, —$C(CH_3)=CH$—$CH_2$—, —$CH=C(CH_3)$—$CH_2$—, —$C(CH_3)=C(CH_3)$—, —$C(CH_2CH_3)=CH$—, —$CH=CH$—$CH_2$—$CH_2$—$CH_2$—, —$CH_2$—$CH=CH$—$CH_2$—$CH_2$—, —$CH=CH$—$CH$—$CH_2$—$CH_2$— and —$CH=CH$—$CH$—$CH=CH_2$—. Preferred $C_{2-8}$ alkynylene groups are selected from the group consisting of —$C\equiv C$—, —$C\equiv C$—$CH_2$—, —$C\equiv C$—$CH_2$—$CH_2$—, —$C\equiv C$—$CH(CH_3)$—, —$CH_2$—$C\equiv C$—$CH_2$—, —$C\equiv C$—$C\equiv C$—, —$C\equiv C$—$C(CH_3)_2$—, —$C\equiv C$—$CH_2$—$CH_2$—$CH_2$—, —$CH_2$—$C\equiv C$—$CH_2$—$CH_2$—, —$C\equiv C$—$C\equiv C$—$CH_2$— and —$C\equiv C$—$CH_2$—$C\equiv C$—.

In relation to "aliphatic residue" and "aliphatic group" the term "mono- or polysubstituted" refers in the sense of this invention, with respect to the corresponding residues or groups, to the single substitution or multiple substitution, e.g. disubstitution, trisubstitution and tetrasubstitution, of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue$)_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-8}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$. The term "polysubstituted" with respect to polysubstituted residues and groups includes the polysubstitution of these residues and groups either on different or on the same atoms, for example trisubstituted on the same carbon atom, as in the case of $CF_3$ or $CH_2CF_3$, or at various points, as in the case of CH(OH)—CH=CH—$CHCl_2$. A substituent can if appropriate for its part in turn be mono- or polysubstituted. The multiple substitution can be carried out using the same or using different substituents.

In relation to "cycloaliphatic residue" and "heterocycloaliphatic residue" the term "mono- or polysubstituted" refers in the sense of this invention, with respect to the corresponding residues, to the single substitution or multiple substitution, e.g. disubstitution, trisubstitution and tetrasubstitution, of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$. The term "polysubstituted" with respect to polysubstituted residues and groups includes the polysubstitution of these residues and groups either on different or on the same atoms, for example disubstituted on the same carbon atom, as in the case of 1,1-difluorocyclohexyl, or at various points, as in the case of 1-chloro-3-fluorocyclohexyl. A substituent can if appropriate for its part in turn be mono- or polysubstituted. The multiple substitution can be carried out using the same or using different substituents.

Preferred substituents of "aliphatic residue" and "aliphatic group" are selected from the group consisting of F, Cl, Br, I, $NO_2$, $NH_2$, an $NH(C_{1-4}$ aliphatic residue), an $N(C_{1-4}$ aliphatic residue)$_2$, =O, OH, $OCF_3$, a O—$C_{1-4}$-aliphatic residue, SH, $SCF_3$, a S—$C_{1-4}$-aliphatic residue, a S(=O)$_2$—$C_{1-4}$-aliphatic residue, a S(=O)$_2$—NH—$C_{1-4}$-aliphatic residue, CN, $CF_3$, a $C_{1-4}$-aliphatic residue, a C(=O)—$C_{1-4}$-aliphatic residue, a C(=O)—O—$C_{1-4}$-aliphatic residue, $CONH_2$, a C(=O)—NH($C_{1-4}$ aliphatic residue), and a C(=O)—N($C_{1-4}$ aliphatic residue)$_2$.

Preferred substituents of "cycloaliphatic residue" and "heterocycloaliphatic residue" are selected from the group consisting of F, Cl, Br, I, $NO_2$, $NH_2$, an $NH(C_{1-4}$ aliphatic residue), an $N(C_{1-4}$ aliphatic residue)$_2$, =O, OH, $OCF_3$, a O—$C_{1-4}$-aliphatic residue, SH, $SCF_3$, a S—$C_{1-4}$-aliphatic residue, a S(=O)$_2$—$C_{1-4}$-aliphatic residue, a S(=O)$_2$—NH—$C_{1-4}$-aliphatic residue, CN, $CF_3$, a $C_{1-4}$-aliphatic residue, a C(=O)—$C_{1-4}$-aliphatic residue, a C(=O)—O—$C_{1-4}$-aliphatic residue, $CONH_2$, a C(=O)—NH($C_{1-4}$ aliphatic residue), and a C(=O)—N($C_{1-4}$ aliphatic residue)$_2$.

In relation to "aryl" and "heteroaryl" the term "mono- or polysubstituted" refers in the sense of this invention to the single substitution or multiple substitution, e.g. disubstitution, trisubstitution and tetrasubstitution, of one or more hydrogen atoms each independently of one another by at least one substituent selected from the group consisting of F, Cl, Br, I, $NO_2$, $NH_2$,

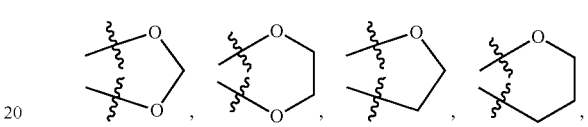

an $NH(C_{1-4}$ aliphatic residue), an $N(C_{1-4}$ aliphatic residue)$_2$, an NH—C(=O)—$C_{1-4}$ aliphatic residue, an NH—S(=O)$_2$—$C_{1-4}$ aliphatic residue, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, C(=O)H, C(=O)OH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—$NH_2$, a C(=O)—NH($C_{1-4}$ aliphatic residue), and a C(=O)—N($C_{1-4}$ aliphatic residue)$_2$ on one or if appropriate different atoms, wherein a substituent can if appropriate for its part in turn be mono- or polysubstituted. The multiple substitution is carried out employing the same or using different substituents.

Preferred substituents of "aryl" and "heteroaryl" are selected from the group consisting of F, Cl, Br, I, $NO_2$, $NH_2$,

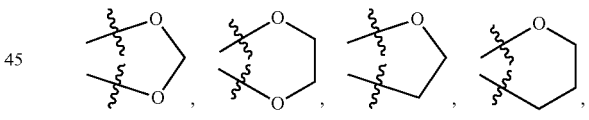

an $NH(C_{1-4}$ aliphatic residue), an $N(C_{1-4}$ aliphatic residue)$_2$, an NH—C(=O)—$C_{1-4}$ aliphatic residue, an NH—S(=O)$_2$—$C_{1-4}$ aliphatic residue, OH, $OCF_3$, a O—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—NH—$C_{1-4}$-aliphatic residue, CN, $CF_3$, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, $CONH_2$, a C(=O)—NH($C_{1-4}$ aliphatic residue), a C(=O)—N($C_{1-4}$ aliphatic residue)$_2$, aryl, preferably phenyl, or benzyl, in each case unsubstituted or mono- or polysubstituted with at least one substituent selected from the group consisting of F, Cl, Br, I, CN, $CF_3$, $CH_3$, $C_2H_5$, iso-propyl, tert.-butyl, C(=O)—OH, C(=O)—$CH_3$, C(=O)—$C_2H_5$, C(=O)—O—$CH_3$ and C(=O)—O—$C_2H_5$, O—$CH_3$, $OCF_3$, O—$CH_2$—OH, O—$CH_2$—O—$CH_3$, SH, S—$CH_3$, $SCF_3$, $NO_2$, $NH_2$, $N(CH_3)_2$, $N(CH_3)(C_2H_5)$ and $N(C_2H_5)_2$, heteroaryl, preferably pyridyl, thienyl, furyl, thiazolyl or oxazolyl, in each case unsubstituted or mono- or polysubstituted with at least one substituent selected from the group consisting of F, Cl, Br, I, CN, $CF_3$, $CH_3$, $C_2H_5$, iso-propyl, tert.-butyl, C(=O)—OH, C(=O)—$CH_3$, C(=O)—$C_2H_5$, C(=O)—O—$CH_3$ and C(=O)—O—$C_2H_5$, O—$CH_3$, $OCF_3$, O—$CH_2$—OH, O—$CH_2$—O—$CH_3$, SH, S—$CH_3$, $SCF_3$, $NO_2$, $NH_2$, $N(CH_3)_2$, $N(CH_3)(C_2H_5)$ and $N(C_2H_5)_2$.

The compounds according to the invention are defined by substituents, for example by $R^1$, $R^2$ and $R^3$ (1$^{st}$ generation substituents) which are for their part if appropriate substituted (2$^{nd}$ generation substituents). Depending on the definition, these substituents of the substituents can for their part be resubstituted (3$^{rd}$ generation substituents). If, for example, $R^1$=a $C_{1-10}$ aliphatic residue (1$^{st}$ generation substituent), then the $C_{1-4}$ aliphatic residue can for its part be substituted, for example with a NH—$C_{1-4}$ aliphatic residue (2$^{nd}$ generation substituent). This produces the functional group $R^1$=($C_{1-10}$ aliphatic residue-NH—$C_{1-4}$ aliphatic residue). The NH—$C_{1-4}$ aliphatic residue can then for its part be resubstituted, for example with Cl (3$^{rd}$ generation substituent). Overall, this produces the functional group $R^1$=$C_{1-10}$ aliphatic residue-NH—$C_{1-4}$ aliphatic residue, wherein the $C_{1-4}$ aliphatic residue of the NH—$C_{1-4}$ aliphatic residue is substituted by Cl.

However, in a preferred embodiment, the 3$^{rd}$ generation substituents may not be resubstituted, i.e. there are then no 4$^{th}$ generation substituents.

In another preferred embodiment, the 2$^{nd}$ generation substituents may not be resubstituted, i.e. there are then not even any 3$^{rd}$ generation substituents. In other words, in this embodiment, in the case of general formula (I), for example, the functional groups for $R^1$ to $R^7$ can each if appropriate be substituted; however, the respective substituents may then for their part not be resubstituted.

In some cases, the compounds according to the invention are defined by substituents which are or carry an aryl or heteroaryl residue, respectively unsubstituted or mono- or polysubstituted, or which form together with the carbon atom(s) or heteroatom(s) connecting them, as the ring member or as the ring members, a ring, for example an aryl or heteroaryl, in each case unsubstituted or mono- or polysubstituted. Both these aryl or heteroaryl residues and the (hetero)aromatic ring systems formed in this way can if appropriate be condensed with a cycloaliphatic, preferably a $C_{3-6}$ cycloaliphatic residue, or heterocycloaliphatic residue, preferably a 3 to 6 membered heterocycloaliphatic residue, or with aryl or heteroaryl, e.g. with a $C_{3-6}$ cycloaliphatic residue such as cyclopentyl, or a 3 to 6 membered heterocycloaliphatic residue such as morpholinyl, or an aryl such as phenyl, or a heteroaryl such as pyridyl, wherein the cycloaliphatic or heterocycloaliphatic residues, aryl or heteroaryl residues condensed in this way can for their part be respectively unsubstituted or mono- or polysubstituted.

In some cases, the compounds according to the invention are defined by substituents which are or carry a cycloaliphatic residue or a heterocycloaliphatic residue, respectively, in each case unsubstituted or mono- or polysubstituted, or which form together with the carbon atom(s) or heteroatom(s) connecting them, as the ring member or as the ring members, a ring, for example a cycloaliphatic or a heterocycloaliphatic ring system. Both these cycloaliphatic or heterocycloaliphatic ring systems and the (hetero)cycloaliphatic ring systems formed in this manner can if appropriate be condensed with aryl or heteroaryl or with a cycloaliphatic residue, preferably a $C_{3-6}$ cycloaliphatic residue, or a heterocycloaliphatic residue, preferably a 3 to 6 membered heterocycloaliphatic residue, e.g. with an aryl such as phenyl, or a heteroaryl such as pyridyl, or a cycloaliphatic residue such as cyclohexyl, or a heterocycloaliphatic residue such as morpholinyl, wherein the aryl or heteroaryl residues or cycloaliphatic or heterocycloaliphatic residues condensed in this way can for their part be respectively unsubstituted or mono- or polysubstituted.

Within the scope of the present invention, the symbol

used in the formulae denotes a link of a corresponding residue to the respective superordinate general structure.

If a residue occurs multiply within a molecule, then this residue can have respectively different meanings for various substituents: if, for example, both $R^2$ and $R^3$ denote a 3 to 6 membered heterocycloaliphatic residue, then the 3 to 6 membered heterocycloaliphatic residue can e.g. represent morpholinyl for $R^2$ and can represent piperazinyl for $R^3$.

The term "salts of physiologically acceptable acids" refers in the sense of this invention to salts of the respective active ingredient with inorganic or organic acids which are physiologically acceptable—in particular when used in human beings and/or other mammals. Hydrochloride is particularly preferred. Examples of physiologically acceptable acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

The term "salts of physiologically acceptable bases" refers in the sense of this invention to salts of the respective compound according to the invention—as an anion, e.g. upon deprotonation of a suitable functional group—with at least one cation or base—preferably with at least one inorganic cation—which are physiologically acceptable—in particular when used in human beings and/or other mammals. Particularly preferred are the salts of the alkali and alkaline earth metals, in particular (mono-) or (di)sodium, (mono-) or (di) potassium, magnesium or calcium salts, but also ammonium salts $[NH_xR_{4-x}]^+$, in which x=0, 1, 2, 3 or 4 and R represents a branched or unbranched $C_{1-4}$ aliphatic residue.

Preferred embodiments of the compound according to general formula (I) have general formulae (Ia), (Ib), (Ic) or (Id):

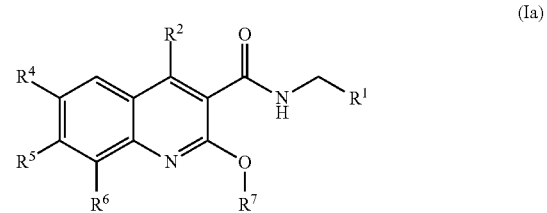

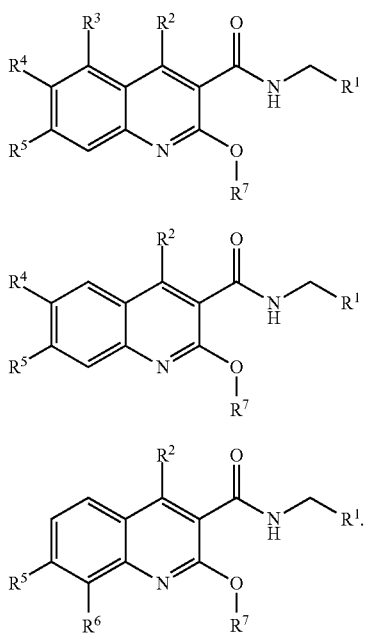

Another preferred embodiment of present invention is a compound according to general formula (I), wherein $R^1$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
  and wherein the $C_{3-10}$-cycloaliphatic residue or the 3 to 10 membered heterocycloaliphatic residue may in each case optionally bridged via a $C_{1-5}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

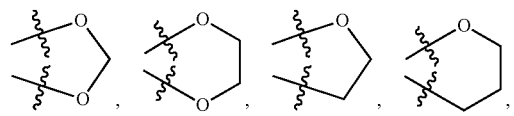

benzyl, phenyl, thienyl, pyridyl, furyl, thiazolyl and oxazolyl,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
  and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN and C(=O)—OH, $R^2$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted, preferably represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and an O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, $R^3$, $R^4$, $R^5$ and $R^6$ each independently of one another represent H; F; Cl; Br; I; CN; $CF_3$; $OCF_3$; $SCF_3$; C(=O)H; C(=O)—OH; C(=O)—$NH_2$; $S(=O)_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—$S(=O)_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^3$, $R^4$, $R^5$ and $R^6$ is ≠H, $R^7$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^7$ denotes a 3 to 10 membered heterocycloaliphatic residue, the 3 to 10 membered heterocycloaliphatic residue is linked via a carbon atom.

In a preferred embodiment of the compound according to general formula (I), the residue $R^1$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—C$_2$H$_5$, a C$_{3-6}$ cycloaliphatic residue, a 3 to 6 membered heterocycloaliphatic residue,

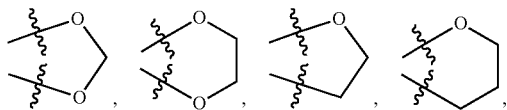

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the aryl or the heteroaryl residue may in each case be optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN and C(=O)—OH.

In a further preferred embodiment of the compound according to general formula (I), the residue R$^1$ represents the partial structure (T1)

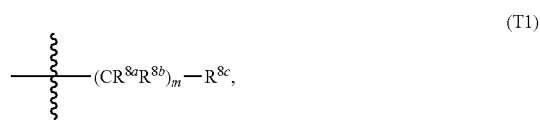

(T1)

wherein m denotes 0, 1, 2, 3 or 4, preferably denotes 0, 1, or 2,

R$^{8a}$ and R$^{8b}$ each independently of one another represent H, F, Cl, Br, I, NO$_2$, NH$_2$, a NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$ aliphatic residue or C(=O)—OH, or together denote =O, preferably each independently of one another represent H, F, Cl, Br, I, NH$_2$, a NH(C$_{1-4}$ aliphatic residue), a N(C$_{1-4}$ aliphatic residue)$_2$, OH, O—C$_{1-4}$ aliphatic residue or a C$_{1-4}$ aliphatic residue, more preferably each independently of one another represent H, F, Cl, Br, I, an O—C$_{1-4}$ aliphatic residue or a C$_{1-4}$ aliphatic residue, even more preferably each independently of one another represent H, F, an O—C$_{1-4}$ aliphatic residue or a C$_{1-4}$ aliphatic residue, and R$^{8c}$ denotes a C$_{1-4}$ aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes a C$_{3-10}$-cycloaliphatic residue or a 3 to 10 membered heterocycloaliphatic residue, preferably when m is ≠0, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes—preferably when m is=0—an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

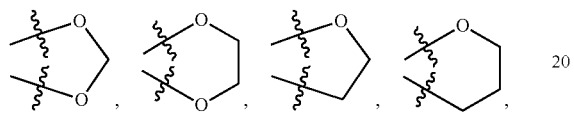

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, OF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH.

Preferably,

R$^1$ represents the partial structure (T1), wherein m denotes 0, 1, or 2,

R$^{8a}$ and R$^{8b}$ each independently of one another represent H, F, Cl, Br, I, an O—C$_{1-4}$ aliphatic residue or a C$_{1-4}$ aliphatic residue, preferably each independently of one another represent H, F, a O—C$_{1-2}$ aliphatic residue or a C$_{1-2}$ aliphatic residue, and R$^{8c}$ denotes a C$_{1-4}$ aliphatic residue, unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue and C(=O)—OH, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue and C(=O)—OH, or denotes—preferably when m is=0—an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue, benzyl, phenyl, thienyl, pyridyl, furyl, thiazolyl or oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue and C(=O)—OH.

More preferably,

R$^1$ represents the partial structure (T1), wherein m denotes 0, 1, or 2,

R$^{8a}$ and R$^{8b}$ each independently of one another represent H, F, Cl, Br, I, an O—C$_{1-4}$ aliphatic residue or a C$_{1-4}$ aliphatic residue, preferably each independently of one another represent H, F, a O—C$_{1-2}$ aliphatic residue or a C$_{1-2}$ aliphatic residue, and R$^{8c}$ denotes a C$_{1-4}$ aliphatic residue, unsubstituted or mono- or polysubstituted with at least one substituent selected from the group consisting of F, Cl, Br, I, an O—C$_{1-4}$ aliphatic residue, CF$_3$, and a C$_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted $O$—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an $O$—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted $O$—$C_{1-4}$-aliphatic residue, or denotes—preferably when m is=0—an aryl or heteroaryl, in each case unsubstituted or mono- or polysubstituted with at least one substituent selected from the group consisting of F, Cl, Br, I, OH, an $O$—$C_{1-4}$ aliphatic residue, $OCF_3$, $CF_3$, CN, a $C_{1-4}$-aliphatic residue, $C(=O)$—$CH_3$, $C(=O)$—$C_2H_5$, $C(=O)$—$O$—$CH_3$ and $C(=O)$—$O$—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an $O$—$C_{1-4}$ aliphatic residue, $OCF_3$, $CF_3$, CN, a $C_{1-4}$-aliphatic residue, $C(=O)$—$CH_3$, $C(=O)$—$C_2H_5$, $C(=O)$—$O$—$CH_3$ and $C(=O)$—$O$—$C_2H_5$, preferably with at least one substituent selected from the group consisting of F, Cl, $CH_3$, $O$—$CH_3$, $CF_3$ and $OCF_3$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an $O$—$C_{1-4}$ aliphatic residue, $OCF_3$, $CF_3$ a $C_{1-4}$-aliphatic residue and $C(=O)$—OH.

In a further preferred embodiment of the compound according to general formula (I), the residue $R^1$ represents the partial structure (T1), wherein m is 0, 1 or 2 and $R^{8a}$ and $R^{8b}$ each independently of one another represent H, F, a $O$—$C_{1-4}$ aliphatic residue or a $C_{1-4}$ aliphatic residue; preferably H, F, $CH_3$ or $OCH_3$;

$R^{8c}$ denotes a $C_{1-4}$ aliphatic residue, unsubstituted or mono- or polysubstituted with at least one substituent selected from the group consisting of F, Cl, Br, I, an unsubstituted $O$—$C_{1-4}$ aliphatic residue, $CF_3$, and an unsubstituted $C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted $O$—$C_{1-4}$ aliphatic residue, $CF_3$, and an unsubstituted $C_{1-4}$-aliphatic residue, or wherein m is 0, $R^{8a}$ and $R^{8b}$ each independently of one another represent H, F, a $O$—$C_{1-4}$ aliphatic residue or a $C_{1-4}$ aliphatic residue; preferably H, F, $CH_3$ or $OCH_3$; and $R^{8c}$ denotes an aryl or heteroaryl, in each case unsubstituted or mono- or polysubstituted with at least one substituent selected from the group consisting of F, Cl, Br, I, OH, an $O$—$C_{1-4}$ aliphatic residue, $OCF_3$, $CF_3$, CN, a $C_{1-4}$-aliphatic residue, $C(=O)$—$CH_3$, $C(=O)$—$C_2H_5$, $C(=O)$—$O$—$CH_3$, $C(=O)$—$O$—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an $O$—$C_{1-4}$ aliphatic residue, $OCF_3$, $CF_3$, CN, a $C_{1-4}$-aliphatic residue, $C(=O)$—$CH_3$, $C(=O)$—$C_2H_5$, $C(=O)$—$O$—$CH_3$ and $C(=O)$—$O$—$C_2H_5$, preferably with at least one substituent selected from the group consisting of F, Cl, $CH_3$, $O$—$CH_3$, $CF_3$ and $OCF_3$.

Particularly preferred is a compound according to general formula (I) which has the following general formula (Ie):

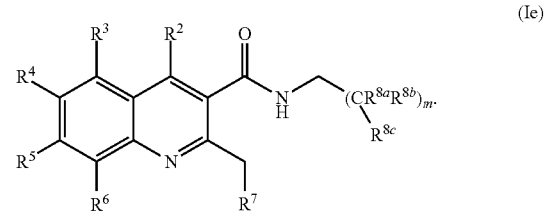

(Ie)

In a preferred embodiment of the compound according to general formula (I), the residue $R^2$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a $O$—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted.

Preferably, $R^2$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a $O$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted $O$—$C_{1-4}$-aliphatic residue, a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a $O$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted $O$—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

More preferably, $R^2$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

Even more preferably, $R^2$ represents H; F; Cl; Br; I; CN; $CF_3$; $NO_2$; $OCF_3$; $SCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; S-Ethyl; cyclopropyl, cyclobutyl, cyclopentyl, and cyclohexyl.

Still more preferably, $R^2$ is selected from the group consisting of H; F; Cl; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$;

In particular, $R^2$ is selected from the group consisting of H; F; Cl; $CF_3$; $CH_3$; $C_2H_5$, iso-propyl; cyclopropyl; and O—$CH_3$;

In a particular preferred embodiment of the compound according to general formula (I), the residue $R^2$ is ≠H.

In a preferred embodiment of the compound according to general formula (I), the residues $R^3$, $R^4$, $R^5$ and $R^6$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^3$, $R^4$, $R^5$ and $R^6$ is ≠H.

Preferably, $R^3$, $R^4$, $R^5$ and $R^6$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^3$, $R^4$, $R^5$ and $R^6$ is ≠H.

More preferably, $R^3$, $R^4$, $R^5$ and $R^6$ each independently of one another represent H; F; Cl; Br; I; CN; $CF_3$; $OCF_3$; $SCF_3$; C(=O)H; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a S—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue, unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^3$, $R^4$, $R^5$ and $R^6$ is ≠H.

In a further preferred embodiment of the present invention $R^3$, $R^4$, $R^5$ and $R^6$ each independently of one another are selected from the group consisting of H; F; Cl; Br; I; $NO_2$; $CF_3$; CN; $OCF_3$; $SCF_3$; a (C=O)—$C_{1-4}$ aliphatic residue, a $C_{1-4}$ aliphatic residue, O—$C_{1-4}$ aliphatic residue, a 5-$C_{1-4}$ aliphatic residue, wherein the $C_{1-4}$-aliphatic residue in each case may be unsubstituted or mono- or polysubstituted with at least one substituent selected from the group consisting of F, Cl, and O—$CH_3$;

preferably on the condition that at least one of $R^3$, $R^4$, $R^5$ and $R^6$ is ≠H.

Preferably, $R^3$, $R^4$, $R^5$ and $R^6$ each independently of one another are selected from the group consisting of H; F; Cl; Br; I; $NO_2$; $CF_3$; CN; $OCF_3$; $SCF_3$; methyl; ethyl; n-propyl; iso-propyl; n-butyl; sec.-butyl; tert.-butyl; cyclopropyl; C(=O)-methyl; C(=O)-ethyl; (C=O)-isopropyl; (C=O)-t-butyl; O-methyl; O-ethyl; O-isopropyl; O-t-butyl; O—$(CH_2)_2$—O—$CH_3$; S-Methyl; S-Ethyl;

preferably on the condition that at least one of $R^3$, $R^4$, $R^5$ and $R^6$ is ≠H.

In particular, $R^3$, $R^4$, $R^5$ and $R^6$ are each independently of one another are selected from the group consisting of H; F; Cl; Br; I; $NO_2$; $CF_3$; CN; (C=O)-methyl; (C=O)-ethyl; (C=O)-isopropyl; (C=O)-t-butyl; methyl; ethyl; isopropyl; t-butyl; O-methyl; O-Ethyl; O-isopropyl; O-t-butyl; $OCF_3$; S-methyl; S-ethyl; and $SCF_3$;

preferably on the condition that at least one of $R^3$, $R^4$, $R^5$ and $R^6$ is ≠H.

More particularly, $R^3$, $R^4$, $R^5$ and $R^6$ are each independently of one another selected from the group consisting of H; F; Cl; Br; $CF_3$; CN; $OCF_3$ and $NO_2$;

preferably on the condition that at least one of $R^3$, $R^4$, $R^5$ and $R^6$ is ≠H.

Most preferred, $R^3$, $R^4$ and $R^6$ each independently of one another are selected from the group consisting of H and F; and $R^5$ denotes F; Br; $CF_3$; $OCF_3$; CN; or $NO_2$;

In a particular preferred embodiment of the compound according to general formula (I) at least one of the residues $R^3$, $R^4$, $R^5$ and $R^6$ is ≠H.

In a preferred embodiment of the compound according to general formula (I), the residue $R^7$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^7$ denotes a 3 to 10 membered heterocycloaliphatic residue, the 3 to 10 membered heterocycloaliphatic residue is linked via a carbon atom.

In a further preferred embodiment of the compound according to general formula (I), the residue $R^7$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, CN, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, a $C_{1-4}$-aliphatic residue, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, and a $C_{1-4}$-aliphatic residue.

on the condition that if $R^7$ denotes a 3 to 10 membered heterocycloaliphatic residue, the 3 to 10 membered heterocycloaliphatic residue is linked via a carbon atom.

Preferably, $R^7$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a C(=O)—O—$C_{1-4}$-aliphatic residue, a S—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue.

on the condition that if $R^7$ denotes a 3 to 10 membered heterocycloaliphatic residue, the 3 to 10 membered heterocycloaliphatic residue is linked via a carbon atom.

More preferably, $R^7$ denotes a $C_{1-8}$-aliphatic residue, preferably a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, $CF_3$, a C(=O)—O—$C_{1-4}$-aliphatic residue, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue is bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue.

Even more preferably, $R^7$ denotes a $C_{1-8}$-aliphatic residue, preferably a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue is in each case bridged via a unsubstituted $C_{1-8}$ aliphatic group, preferably an unsubstituted $C_{1-4}$ aliphatic group.

Still more preferably, $R^7$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue wherein the $C_{1-4}$-aliphatic residue in each case is unsubstituted, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue.

and wherein the $C_{3-10}$-cycloaliphatic residue or the 3 to 10 membered heterocycloaliphatic residue is in each case bridged via a unsubstituted $C_{1-4}$ aliphatic group In particular, $R^7$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue wherein the $C_{1-4}$-aliphatic residue in each case is unsubstituted.

Most preferred, $R^7$ denotes a $C_{1-6}$-aliphatic residue, unsubstituted or mono- or polysubstituted with at least one substituent selected from the group consisting of F, $CF_3$, Cl, OH, and O-methyl.

Preferred is also a compound according to general formula (I), wherein
R¹ represents the partial structure (T1),

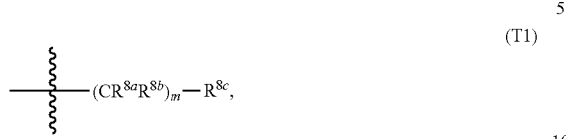
(T1)

wherein
m is 0, 1 or 2 and
R$^{8a}$ and R$^{8b}$ each independently of one another represent H, F, a O—C$_{1-4}$ aliphatic residue or a C$_{1-4}$ aliphatic residue; preferably H, F, CH$_3$ or OCH$_3$;
R$^{8c}$ denotes a C$_{1-4}$ aliphatic residue, unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue,
or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue,
or
wherein
m is 0,
R$^{8a}$ and R$^{8b}$ each independently of one another represent H, F, a O—C$_{1-4}$ aliphatic residue or a C$_{1-4}$ aliphatic residue; preferably H, F, CH$_3$ or OCH$_3$; and
R$^{8c}$ denotes an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$,
R$^2$ is selected from the group consisting of H; F; Cl; CF$_3$; CH$_3$; C$_2$H$_5$, iso-propyl; cyclopropyl; and O—CH$_3$;
R$^3$, R$^4$, R$^5$ and R$^6$ are each independently of one another selected from the group consisting of H; F; Cl; Br; CF$_3$; CN; OCF$_3$ and NO$_2$;
preferably on the condition that at least one of R$^3$, R$^4$, R$^5$ and R$^6$ is ≠H,
R$^7$ denotes a C$_{1-6}$-aliphatic residue, unsubstituted or mono- or polysubstituted with at least one substituent selected from the group consisting of F, Cl, Br, I, OH, =O, an O—C$_{1-4}$-aliphatic residue, a C(=O)—O—C$_{1-4}$-aliphatic residue, OCF$_3$, SH, SCF$_3$, a S—C$_{1-4}$-aliphatic residue, CF$_3$, and a C$_{1-4}$-aliphatic residue
wherein the C$_{1-4}$-aliphatic residue in each case is unsubstituted.

Particularly preferred is also a compound according to general formula (I), wherein
R¹ represents aryl, preferably phenyl, or heteroaryl, preferably pyridyl or thienyl, in each case unsubstituted or mono- or disubstituted with at least one substituent selected from the group consisting of F, Cl, Br, I, OH, OCH$_3$, OCF$_3$, CF$_3$, CN, and CH$_3$,
preferably represents phenyl, unsubstituted or mono- or disubstituted with at least one substituent selected from the group consisting of F, Cl, Br, I, OH, OCH$_3$, OCF$_3$, CF$_3$, CN, and CH$_3$;
R$^2$ is selected from the group consisting of H, F, Cl, CF$_3$, CH$_3$, C$_2$H$_5$, iso-propyl, cyclopropyl, and O—CH$_3$; preferably is selected from the group consisting of CH$_3$, C$_2$H$_5$, OCH$_3$ and CF$_3$;
R$^3$, R$^4$, R$^5$ and R$^6$ are each independently of one another selected from the group consisting of H, F, Cl, Br, CF$_3$, CN, OCF$_3$ and NO$_2$;
preferably on the condition that at least one of R$^3$, R$^4$, R$^5$ and R$^6$ is ≠H, more preferably on the condition that R$^5$ is ≠H;
R$^7$ denotes a saturated C$_{1-4}$-aliphatic residue, unsubstituted or mono- or disubstituted with at least one substituent selected from the group consisting of F, Cl, Br, I, OH, O—CH$_3$, OCF$_3$, SCF$_3$, and CF$_3$.

Especially particularly preferred are compounds according to general formula (I) selected from the group comprising:
1  N-(3,3-dimethyl-butyl)-2-methoxy-4-methyl-7-(trifluoromethyl)-quinoline-3-carboxylic acid amide;
2  2-ethoxy-4-methyl-N-(thiophene-2-yl-methyl)-7-(trifluoromethyl)-quinoline-3-carboxylic acid amide;
3  2-ethoxy-N-[(4-fluorophenyl)-methyl]-4-methyl-7-(trifluoromethyl)-quinoline-3-carboxylic acid amide;
4  N-[(3-fluorophenyl)-methyl]-2-methoxy-4-methyl-7-(trifluoromethyl)-quinoline-3-carboxylic acid amide;
5  N-[(4-fluorophenyl)-methyl]-2-methoxy-4-methyl-7-(trifluoromethyl)-quinoline-3-carboxylic acid amide;
6  2-ethoxy-N-[(3-fluorophenyl)-methyl]-4-methyl-7-(trifluoromethyl)-quinoline-3-carboxylic acid amide;
7  N-[(3-fluorophenyl)-methyl]-2-(2-methoxy-ethoxy)-4-methyl-7-(trifluoromethyl)-quinoline-3-carboxylic acid amide;
8  N-[(4-fluorophenyl)-methyl]-2-(2-methoxy-ethoxy)-4-methyl-7-(trifluoromethyl)-quinoline-3-carboxylic acid amide;
9 N-[(3-fluorophenyl)-methyl]-2-(2-hydroxy-ethoxy)-4-methyl-7-(trifluoromethyl)-quinoline-3-carboxylic acid amide;
10  N-[(3-fluorophenyl)-methyl]-2-isopropoxy-4-methyl-7-(trifluoromethyl)-quinoline-3-carboxylic acid amide;
11  N-[(4-fluorophenyl)-methyl]-2-isopropoxy-4-methyl-7-(trifluoromethyl)-quinoline-3-carboxylic acid amide;
12 2-ethoxy-N-[(3-fluorophenyl)-methyl]-4-methoxy-7-(trifluoromethyl)-quinoline-3-carboxylic acid amide;
13  N-[(3-fluorophenyl)-methyl]-2,4-dimethoxy-7-(trifluoromethyl)-quinoline-3-carboxylic acid amide;
14 2-ethoxy-N-[(4-fluorophenyl)-methyl]-4-methoxy-7-(trifluoromethyl)-quinoline-3-carboxylic acid amide;
15  2-ethoxy-6,7-difluoro-N-[(3-fluorophenyl)-methyl]-4-methoxy-quinoline-3-carboxylic acid amide;
16  N-[(4-fluorophenyl)-methyl]-2,4-dimethoxy-7-(trifluoromethyl)-quinoline-3-carboxylic acid amide;
17  6,7-difluoro-N-[(3-fluorophenyl)-methyl]-2,4-dimethoxy-quinoline-3-carboxylic acid amide;
18  7-fluoro-N-[(3-fluorophenyl)-methyl]-2-methoxy-4-methyl-quinoline-3-carboxylic acid amide;

19 N-[(3-fluoro-4-methyl-phenylmethyl]-2-methoxy-4-methyl-7-(trifluoromethyl)-quinoline-3-carboxylic acid amide;
20 2-ethoxy-N-[(3-fluoro-4-methyl-phenylmethyl]-4-methyl-7-(trifluoromethyl)-quinoline-3-carboxylic acid amide;
21 2-methoxy-4-methyl-N-(m-tolyl-methyl)-7-(trifluoromethyl)-quinoline-3-carboxylic acid amide;
22 2-ethoxy-4-methyl-N-(m-tolyl-methyl)-7-(trifluoromethyl)-quinoline-3-carboxylic acid amide;
23 N-[(4-fluoro-3-methyl-phenyl)-methyl]-2-methoxy-4-methyl-7-(trifluoromethyl)-quinoline-3-carboxylic acid amide;
24 2-ethoxy-N-[(4-fluoro-3-methyl-phenylmethyl]-4-methyl-7-(trifluoromethyl)-quinoline-3-carboxylic acid amide;
25 2-methoxy-4-methyl-N-(p-tolyl-methyl)-7-(trifluoromethyl)-quinoline-3-carboxylic acid amide;
26 2-ethoxy-4-methyl-N-(p-tolyl-methyl)-7-(trifluoromethyl)-quinoline-3-carboxylic acid amide;
27 2-ethoxy-4-methyl-N-(4-methyl-pentyl)-7-(trifluoromethyl)-quinoline-3-carboxylic acid amide;
28 2-methoxy-4-methyl-N-(4-methyl-pentyl)-7-(trifluoromethyl)-quinoline-3-carboxylic acid amide;
29 N-(4,4-dimethyl-pentyl)-2-methoxy-4-methyl-7-(trifluoromethyl)-quinoline-3-carboxylic acid amide;
30 N-(4,4-dimethyl-pentyl)-2-ethoxy-4-methyl-7-(trifluoromethyl)-quinoline-3-carboxylic acid amide;
31 7-bromo-2-ethoxy-N-[(4-fluorophenyl)-methyl]-4-methyl-quinoline-3-carboxylic acid amide;
32 7-bromo-2-ethoxy-N-[(3-fluorophenyl)-methyl]-4-methyl-quinoline-3-carboxylic acid amide;
33 7-bromo-N-[(3-fluorophenyl)-methyl]-2-methoxy-4-methyl-quinoline-3-carboxylic acid amide;
34 7-bromo-N-[(4-fluorophenyl)-methyl]-2-methoxy-4-methyl-quinoline-3-carboxylic acid amide;
35 7-cyano-2-ethoxy-N-[(4-fluorophenyl)-methyl]-4-methyl-quinoline-3-carboxylic acid amide;
36 7-cyano-2-ethoxy-N-[(3-fluorophenyl)-methyl]-4-methyl-quinoline-3-carboxylic acid amide;
37 7-cyano-N-[(3-fluorophenyl)-methyl]-2-methoxy-4-methyl-quinoline-3-carboxylic acid amide;
38 7-cyano-N-[(4-fluorophenyl)-methyl]-2-methoxy-4-methyl-quinoline-3-carboxylic acid amide;
39 N-[(3-fluoro-2-methoxy-phenyl)-methyl]-2-methoxy-4-methyl-7-(trifluoromethyl)-quinoline-3-carboxylic acid amide;
40 N-[(3-fluoro-5-methoxy-phenyl)-methyl]-2-methoxy-4-methyl-7-(trifluoromethyl)-quinoline-3-carboxylic acid amide;
41 N-[(5-fluoro-2-methoxy-phenyl)-methyl]-2-methoxy-4-methyl-7-(trifluoromethyl)-quinoline-3-carboxylic acid amide;
42 N-[(3-fluoro-2-hydroxy-phenyl)-methyl]-2-methoxy-4-methyl-7-(trifluoromethyl)-quinoline-3-carboxylic acid amide;
43 N-[(3-fluoro-5-hydroxy-phenyl)-methyl]-2-methoxy-4-methyl-7-(trifluoromethyl)-quinoline-3-carboxylic acid amide;
44 N-[(5-fluoro-2-hydroxy-phenyl)-methyl]-2-methoxy-4-methyl-7-(trifluoromethyl)-quinoline-3-carboxylic acid amide;
45 N-[(3-fluoro-4-hydroxy-phenyl)-methyl]-2-methoxy-4-methyl-7-(trifluoromethyl)-quinoline-3-carboxylic acid amide;
46 7-fluoro-N-[(4-fluorophenyl)-methyl]-2-methoxy-4-methyl-quinoline-3-carboxylic acid amide:
47 5,7-difluoro-N-[(3-fluorophenyl)-methyl]-2-methoxy-4-methyl-quinoline-3-carboxylic acid amide;
48 6,7-difluoro-N-[(3-fluorophenyl)-methyl]-2-methoxy-4-methyl-quinoline-3-carboxylic acid amide;
49 7,8-difluoro-N-[(3-fluorophenyl)-methyl]-2-methoxy-4-methyl-quinoline-3-carboxylic acid amide;
50 N-[(3-fluorophenyl)-methyl]-4-methyl-2-(2,2,2-trifluoro-ethoxy)-7-(trifluoromethyl)-quinoline-3-carboxylic acid amide;
51 N-[(3-fluorophenyl)-methyl]-2-methoxy-4-(trifluoromethyl)-quinoline-3-carboxylic acid amide;
52 2-ethoxy-N-[(3-fluorophenyl)-methyl]-4-(trifluoromethyl)-quinoline-3-carboxylic acid amide; and
53 N-[(3-fluorophenyl)-methyl]-2-isopropoxy-4-(trifluoromethyl)-quinoline-3-carboxylic acid amide;

respectively in the form of the free compounds; the racemate; the enantiomers, diastereomers, mixtures of the enantiomers or diastereomers in any mixing ratio or of an individual enantiomer or diastereomer; or in the form of the salts of physiologically acceptable acids or bases; or in the form of solvates, in particular hydrates.

The substituted compounds according to the invention of the aforementioned general formula (I) and corresponding stereoisomers and also the respective corresponding salts and solvates are toxicologically safe and are therefore suitable as pharmaceutical active ingredients in pharmaceutical compositions.

The present invention therefore further relates to a pharmaceutical composition containing at least one compound according to general formula (I), in each case if appropriate optionally in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a physiologically acceptable salt, or respectively in the form of a corresponding solvate, and also if appropriate optionally at least one pharmaceutically acceptable auxiliary and/or optionally at least one further active ingredient.

These pharmaceutical compositions according to the invention are suitable in particular for the modulation of KCNQ2/3 K$^+$ channels, preferably for KCNQ2/3 K$^+$ channel inhibition and/or KCNQ2/3 K$^+$ channel stimulation, i.e. they exert an agonistic or antagonistic effect.

Likewise, the pharmaceutical compositions according to the invention are preferably suitable for the prophylaxis and/or treatment of disorders and/or diseases which are mediated, at least in part, by KCNQ2/3 K$^+$ channels.

The pharmaceutical composition according to the invention is suitable for administration to adults and children, including toddlers and babies.

The pharmaceutical composition according to the invention may be prepared as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of general formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally may contain further physiologically acceptable pharmaceutical auxiliaries which, for example, can be selected from the group consisting of excipients, fillers, solvents, diluents, surface-active substances, dyes, preservatives, blasting agents, slip additives, lubricants, aromas and binders.

The selection of the physiologically acceptable auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository, in a dissolved form or in a plaster, and further agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention can be prepared with the aid of conventional means, devices, methods and process known in the art, such as are described for example in "Remington's Pharmaceutical Sciences", A. R. Gennaro (Editor), 17$^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula (I) may vary and is for example dependent on the patient's weight or age and also on the type of application, the indication and the severity of the disorder. Conventionally, 0.001 to 100 mg/kg, preferably 0.05 to 75 mg/kg, particularly preferably 0.05 to 50 mg of at least one compound according to the invention are applied per kg of the patient's body weight.

The pharmaceutical composition according to the invention is preferably suitable for the treatment and/or prophylaxis of one or more diseases and/or disorders selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

The pharmaceutical composition according to the invention is suitable particularly preferably for the treatment of pain, more particularly preferably of acute pain, chronic pain, neuropathic pain, visceral pain, inflammatory pain and muscular pain, and most particularly for the treatment of neuropathic pain.

The pharmaceutical composition according to the invention is also preferably suitable for the treatment and/or prophylaxis of epilepsy.

The present invention therefore further relates to at least one compound according to general formula (I) and also if appropriate of one or more pharmaceutically acceptable auxiliaries for use in the modulation of KCNQ2/3 K$^+$ channels, preferably for use in KCNQ2/3 K$^+$ channel inhibition and/or stimulation.

The present invention therefore further relates to at least one compound according to general formula (I) and also if appropriate of one or more pharmaceutically acceptable auxiliaries for use in the prophylaxis and/or treatment of disorders and/or diseases which are mediated, at least in part, by KCNQ2/3 K$^+$ channels.

Preference is given to at least one compound according to general formula (I) and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for use in the prophylaxis and/or treatment of epilepsy.

The present invention therefore further relates to at least one compound according to general formula (I) and also if appropriate of one or more pharmaceutically acceptable auxiliaries for the modulation of KCNQ2/3 K$^+$ channels, preferably for KCNQ2/3 K$^+$ channel inhibition and/or stimulation.

The present invention therefore further relates to at least one compound according to general formula (I) and also if appropriate of one or more pharmaceutically acceptable auxiliaries for the prophylaxis and/or treatment of disorders and/or diseases which are mediated, at least in part, by KCNQ2/3 K$^+$ channels.

Preference is given to at least one compound according to general formula (I) and optionally one or more pharmaceutically acceptable auxiliaries for the prophylaxis and/or treatment of disorders and/or diseases selected from the group consisting of pain, especially pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for the prophylaxis and/or treatment of epilepsy.

Another aspect of the present invention is a method of treatment and/or prophylaxis of disorders and/or diseases, which are mediated, at least in part, by KCNQ2/3 K$^+$ channels, in a mammal, preferably of disorders and/or diseases selected from the group consisting of pain, preferably pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias, which comprises administering an effective amount of at least one compound of general formula (I) to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Annour and Smith (J. Pharm. Exp. Ther. 72, 74 79 (1941)) or by the formalin test (e.g. according to D. Dubuisson et al., Pain 1977, 4, 161-174). The effectiveness against epilepsy can be demonstrated, for example, in the DBA/2 mouse model (De Sarro et al., Naunyn-Schmiedeberg's Arch. Pharmacol. 2001, 363, 330-336).

The compounds according to the invention preferably have a $EC_{50}$ value of not more than 10000 nM or not more than 8000 nM, more preferably not more than 7000 nM or not more than 6000 nM, yet more preferably not more than 5000 nM or not more than 3000 nM, even more preferably not more than 2000 nM or not more than 1000 nM, yet even more preferably not more than 800 nM or not more than 700 nM, still more preferably not more than 600 nM or not more than 500 nM, yet still more preferably not more than 400 nM or not more than 300 nM, most preferably not more than 200 nM or not more than 150 nM and especially not more than 120 nM or not more than 100 nM. Methods for determining the $EC_{50}$ value are known to the person skilled in the art. The $EC_{50}$ value is preferably determined by fluorimetry, particularly preferably as described below under "pharmacological experiments".

The invention further provides processes for the preparation of the substituted compounds according to the invention.

The chemicals and reaction components used in the reactions and schemes described below are available commercially or in each case can be prepared by conventional methods known to the person skilled in the art.

The reactions described can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps described below, as well as the respective purification and/or isolation of intermediate or end products, can be carried out partly or completely under an inert gas atmosphere, preferably under a nitrogen atmosphere.

If the substituted compounds according to the invention of the aforementioned general formula (I) are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

General reaction scheme I (synthesis of precursors P1 and P2):

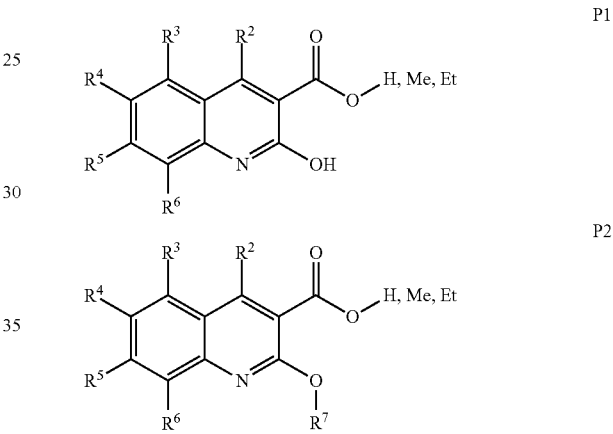

A plurality of syntheses of and synthesis paths to compounds of the general formulae P1 and P2 with a very broad substitution model for residues $R^2$, $R^3$, $R^4$, $R^5$, $R^6$ and $R^7$ are known in the current specialist literature. Previously unknown intermediates of the general formulae P1 and P2 with similar substitution models for residues $R^2$, $R^3$, $R^4$, $R^5$, $R^6$ and $R^7$, as outlined below and whose syntheses are not described in greater detail, can be produced by the person skilled in the art according to these known methods or by combination of the known methods.

General reaction scheme II:

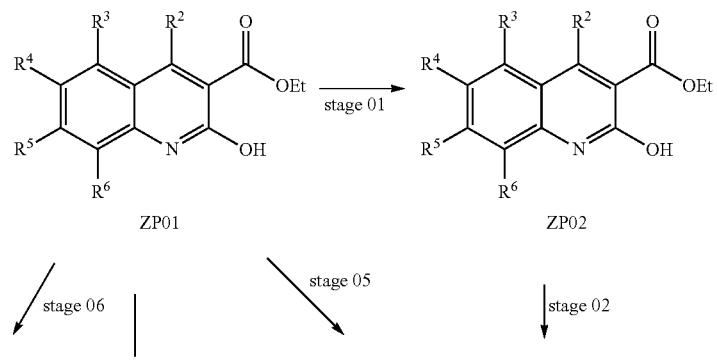

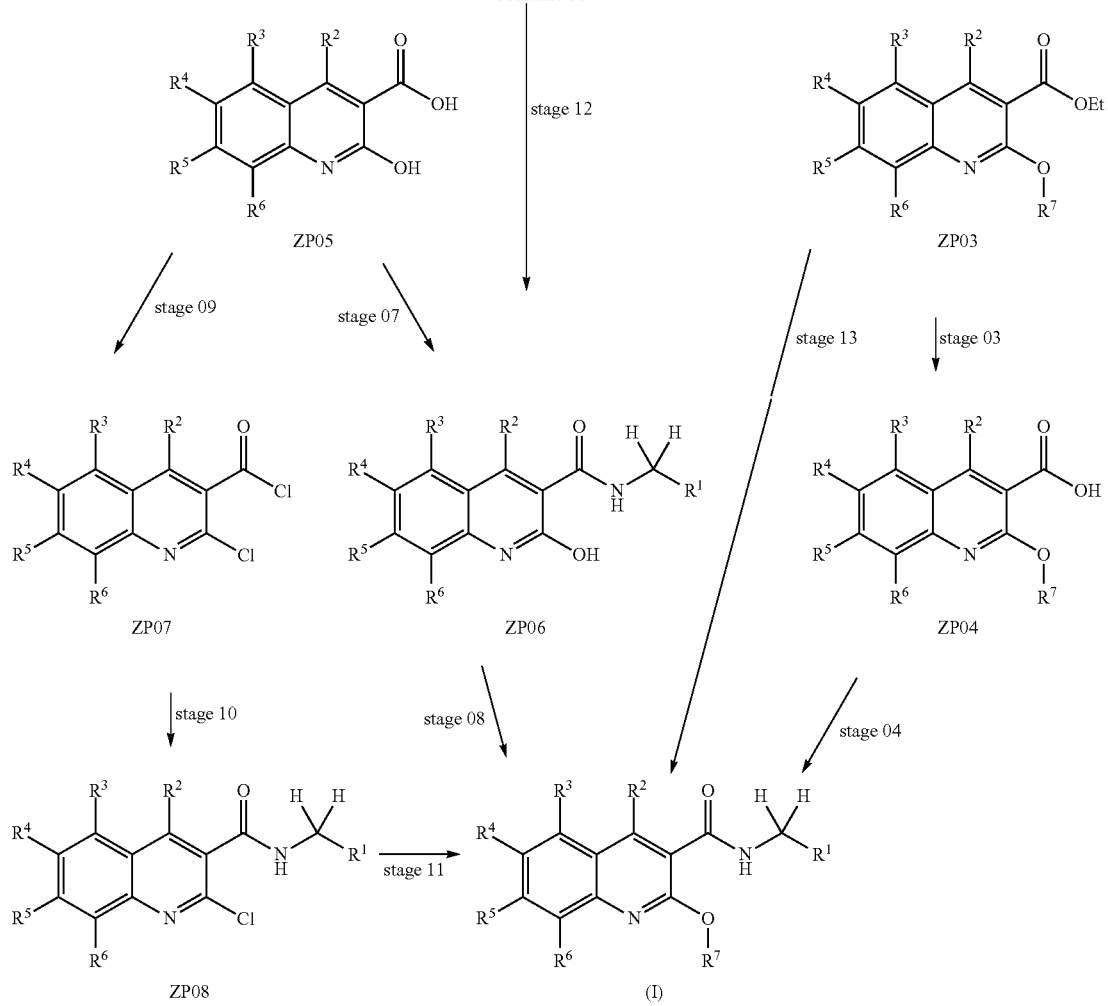

In stage01, 2-quinolones ZP01 can be transformed into 2-chloro-quinolines ZP02 according to methods known to the person skilled in the art, for example, by conversion with phosphoroxychloride.

In stage02 and stage11, 2-chloroquinolines ZP02 or ZP08 can be transformed into the corresponding 2-alkoxy-quinolines ZP03 (stage02) or of the general formula (I) (stage 11) by conversion with alcohols $R^7$—OH according to methods known to the person skilled in the art, for example, using sodium hydride.

In stage03 and stage06, esters ZP01 or ZP03 can be transformed into acids ZP05 or ZP04, respectively, according to methods known to the person skilled in the art, for example, using a base, for example, lithium hydroxide.

In stage04 and stage07, acids ZP04 or ZP05 can be transformed into amides of the general formula (I) or ZP06, respectively, with amines $R^1$—$CH_2$—$NH_2$ according to methods known to the person skilled in the art, for example, using a suitable coupling reagent, for example, HATU.

In stage05 and stage08, 2-hydroxy-quinolines ZP01 or ZP08, respectively, can be transformed into 2-alkoxy-quinolines ZP03 or of the general formula (I), respectively, with compounds of the general formula $R^7$—X, wherein X denotes a leaving group, for example, chlorine, bromine, methane sulphonate or p-toluene sulphonate, according to methods known to the person skilled in the art, for example, with the addition of a base, for example, $K_2CO_3$.

In stage09, quinoline-2-on-3-carboxylic acids ZP05 can be transformed into 2-chloro-quinoline-3-carboxylic acid chlorides ZP07 according to methods known to the person skilled in the art, for example, by conversion with phosphoroxychloride.

In stage10, 2-chloro-quinoline-3-carboxylic acid chlorides ZP07 can be converted to yield amides ZP08 with amines of the general formula $R^1$—$CH_2$—$NH_2$ according to methods known to the person skilled in the art, for example, by conversion in ethanol.

In stage12 and stage 13, quinoline-3-carboxylic acid esters ZP01 or ZP03, respectively, can be converted to yield amides ZP06 or of the general formula (I), respectively, with amines of the general formula $R^1$—$CH_2$—$NH_2$ according to methods known to the person skilled in the art, for example, with the addition of trimethylaluminium.

Thus obtained compounds of the general formula (I) can be further transformed to introduce and/or exchange one or more of the substituents $R^1$, $R^2$, $R^3$, $R^4$ $R^6$ and $R^7$ by simple derivatization reactions known to the person skilled in the art, for example, esterification, ester formation, amide formation, etherification, ether cleavage, substitution or cross-coupling reactions.

The invention will be described hereinafter with the aid of a number of examples. This description is intended merely by way of example and does not limit the general idea of the invention.

EXAMPLES

The indication "equivalents" ("eq.") means molar equivalents, "RT" means room temperature (23±7° C.), "M" is an indication of concentration in mol/l, "aq." means aqueous, "sat." means saturated, "sol." means solution, "conc." means concentrated.

Further abbreviations:
AcOH acetic acid
d days
brine saturated aqueous sodium chloride solution (NaCl sol.)
CC column chromatography on silica gel
dba dibenzylidenaceton
DCM dichloromethane
DIPEA N,N-diisopropylethylamine
DMF N,N-dimethylformamide
DMSO dimethyl sulfoxide
EtOAc ethyl acetate
ether diethyl ether
EtOH ethanol
h hour(s)
$H_2O$ water
HATU O-(7-aza-benzotriazol-1-yl)-N,N,N',N'-tetramethyluroniunnhexafluorophosphate
m/z mass-to-charge ratio
MeOH methanol
MeCN acetonitrile
min minutes
MS mass spectrometry
MW microwave
N/A not available
$NEt_3$ triethylamine
RS reaction solution
THF tetrahydrofuran
TMEDA N,N,N',N'-Tetramethylethylendiannin
Xantphos 4,5-Bis(diphenylphosphino)-9,9-dimethylxanthene The yields of the compounds prepared were not optimized.
All temperatures are uncorrected.
All starting materials which are not explicitly described were either commercially available (the details of suppliers such as for example Acros, Avocado, Aldrich, Bachem, Fluka, Lancaster, Maybridge, Merck, Sigma, TCI, Oakwood, etc. can be found in the Symyx® Available Chemicals Database of MDL, San Ramon, US, or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL, or the SciFinder® Database of the ACS, Washington D.C., US, respectively, for example) or can be prepared using the conventional methods known to the person skilled in the art.

The stationary phase used for the column chromatography was silica gel 60 (0.04-0.063 mm) from E. Merck, Darmstadt.

The mixing ratios of solvents or eluents for chromatography tests are respectively specified in volume/volume.

All the intermediate products and exemplary compounds were analytically characterised by means of $^1$H-NMR spectroscopy. In addition, mass spectrometry tests (MS, m/z [M+H]$^+$) were carried out for all the exemplary compounds and selected intermediate products.

Synthesis of Exemplary Compounds

Synthesis of Example 2

2-ethoxy-4-methyl-N-(thiophene-2-yl-methyl)-7-(trifluoromethyl)-quinoline-3-carboxylic acid amide a) Synthesis of 2-ethoxy-4-methyl-7-(trifluoromethyl)quinoline-3-carboxylic acid ethyl ester 354 mg (2.6 mmol) $K_2CO_3$ was added to a solution of 700 mg (2.3 mmol) 2-hydroxy-4-methyl-7-(trifluoromethyl) quinoline-3-carboxylic acid ethyl ester in DMF (9 ml) and stirred for 60 min at RT. 190 µl (2.3 mmol) iodoethane was then added and the RS was stirred for a further 16 h at RT. The solution was subsequently diluted with water and EtOAc. The organic phase was separated, dried over $MgSO_4$ and concentrated in a vacuum. After CC (EtOAc/hexane 1:3) of the residue, 168 mg (0.5 mmol, 22%) 2-ethoxy-4-methyl-7-(trifluoromethyl)quinoline-3-carboxylic acid ethyl ester was obtained.

b) Synthesis of 2-ethoxy-4-methyl-7-(trifluoromethyl)quinoline-3-carboxylic acid The synthesis of 2-ethoxy-4-methyl-7-(trifluoromethyl) quinoline-3-carboxylic acid is described in the case of the synthesis of Example 3 Section b).

c) Synthesis of 2-ethoxy-4-methyl-N-(thiophene-2-yl-methyl)-7-(trifluoromethyl)-quinoline-3-carboxylic acid amide 53 µl (0.5 mmol) thiophene methane amine, 172 mg (0.5 mmol) HATU and 165 µl (1.2 mmol) $NEt_3$ were added consecutively to a solution of 123 mg (0.4 mmol) 2-ethoxy-4-methyl-7-(trifluoromethyl)quinoline-3-carboxylic acid in THF (3 ml) and thereafter stirred for 16 h at RT. The solution was subsequently diluted with EtOAc and washed with a 4N aq. $NH_4CL$ sol., a 1M aq. $Na_2CO_3$ sol. and brine. The organic phase was dried over $MgSO_4$, filtered through silica gel and concentrated in a vacuum. 116 mg (0.3 mmol, 72%) 2-ethoxy-4-methyl-N-(thiophene-2-yl-methyl)-7-(trifluoromethyl)-quinoline-3-carboxylic acid amide (example 2) was obtained as a residue. MS: m/z 395.1 [M+H]$^+$.

Synthesis of Example 3

2-ethoxy-N-[(4-fluorophenyl)-methyl]-4-methyl-7-(trifluoromethyl)-quinoline-3-carboxylic acid amide a) Synthesis of 2-chloro-4-methyl-7-(trifluoromethyl)quinoline-3-carboxylic acid ethyl ester A solution of 15.0 g (50.1 mmol) 2-hydroxy-4-methyl-7-(trifluoromethyl)quinoline-3-carboxylic acid ethyl ester in $POCl_3$ (46 ml) was heated to 100° C. for 2 h. After cooling of the RS to RT, it was diluted with EtOAc and neutralised with a sat. aq. $NaHCO_3$ sol. The organic phase was separated and washed with brine, dried over $MgSO_4$ and concentrated in a vacuum. 15.4 g (48.5 mmol, 97%) 2-chloro-4-methyl-7-(trifluoromethyl)quinoline-3-carboxylic acid ethyl ester was obtained as a residue. The raw product was further converted without additional purification.

b) Synthesis of 2-ethoxy-4-methyl-7-(trifluoromethyl)quinoline-3-carboxylic acid ethyl ester 1.2 g (17.8 mmol) sodium ethylate was added to a solution of 5.1 g (16.1 mmol) 2-chloro-4-methyl-7-(trifluoromethyl) quinoline-3-carboxylic acid ethyl ester in EtOH (20 ml) at RT. The RS was subsequently heated to 60° C. for 4 h and then stirred for 16 h at RT. The solution was then diluted with water and EtOAc. The organic phase was separated and washed with a 4N aq. NH₄Cl sol., dried over MgSO₄ and concentrated in a vacuum. 5.1 g (15.6 mmol, 97%) 2-ethoxy-4-methyl-7-(trifluoromethyl)quinoline-3-carboxylic acid ethyl ester was obtained as a residue. The raw product was further converted without additional purification.

c) Synthesis of 2-ethoxy-4-methyl-7-(trifluoromethyl)quinoline-3-carboxylic acid 2M aq. LiOH sol. (38 ml) was added to a solution of 5.1 g (15.5 mmol) 2-ethoxy-4-methyl-7-(trifluoromethyl)quinoline-3-carboxylic acid ethyl ester in a MeOH/THF mixture (in each case 38 ml) and subsequently heated to 60° C. for 16 h. The organic solvents were removed as far as possible in a vacuum and the obtained aqueous solution was washed with EtOAc, set at pH 2 with 2M hydrochloric acid and diluted with EtOAc. The organic phase was separated and washed with brine, dried over MgSO₄ and concentrated in a vacuum. 4.4 g (14.7 mmol, 95%) 2-ethoxy-4-methyl-7-(trifluoromethyl)quinoline-3-carboxylic acid was obtained as a residue. The raw product was further converted without additional purification.

d) Synthesis of ethoxy-N-[(4-fluorophenyl)-methyl]-4-methyl-7-(trifluoromethyl)-quinoline-3-carboxylic acid amide 166 µl (1.5 mmol) 4-fluoro-benzylamine, 506 mg (1.3 mmol) HATU and 537 µl (3.9 mmol) NEt₃ were added consecutively to a solution of 400 mg (1.3 mmol) 2-ethoxy-4-methyl-7-(trifluoromethyl)quinoline-3-carboxylic acid in 1,4-dioxane (11 ml) and thereafter stirred for 72 h at 80° C. After cooling to RT, the solution was diluted with EtOAc and washed with a 4N aq. NH₄CL sol., a 2M aq. Na₂CO₃ sol. and brine. The organic phase was dried over MgSO₄ and concentrated in a vacuum. After CC (EA/hexane 1:3) of the residue, 432 mg (1.1 mmol, 80%) ethoxy-N-[(4-fluorophenyl)-methyl]-4-methyl-7-(trifluoromethyl)-quinoline-3-carboxylic acid amide (example compound 3) was obtained. MS: m/z 407.1 [M+H]⁺.

Synthesis of Example 4

N-[(3-fluorophenyl)-methyl]-2-methoxy-4-methyl-7-(trifluoromethyl)-quinoline-3-carboxylic acid amide a) Synthesis of 2-hydroxy-4-methyl-7-(trifluoromethyl) quinoline-3-carboxylic acid 2M aq. LiOH sol. (125 ml) was added to a solution of 15.0 g (50.1 mmol) 2-hydroxy-4-methyl-7-(trifluoromethyl) quinoline-3-carboxylic acid ethyl ester in a MeOH/THF mixture (in each case 175 ml) and the solution was subsequently heated to 60° C. for 16 h. The solution was subsequently concentrated in a vacuum. The residue was taken up with water and adjusted to pH 2 with a 2M hydrochloric acid. Extraction was then performed with EtOAc. The organic phase was washed with brine, dried over MgSO₄ and concentrated in a vacuum. 12.0 g (44.2 mmol, 88%) 2-hydroxy-4-methyl-7-(trifluoromethyl)quinoline-3-carboxylic acid was obtained as a residue. The raw product was further converted without additional purification.

b) Synthesis of 2-chloro-4-methyl-7-(trifluoromethyl)quinoline-3-carboxylic acid chloride A solution of 12.0 g (44.2 mmol, 88%) 2-hydroxy-4-methyl-7-(trifluoromethyl)quinoline-3-carboxylic acid in POCl₃ (41 ml) was stirred for 2 h at 100° C. After cooling to RT, the solution was diluted with toluene (10 ml) and stirred for 10 min at 60° C. The solution was then concentrated in a vacuum. The residue was taken up with water and EtOAc and a 1M aq. NaHCO₃ sol. was added. The organic phase was separated, washed with water and brine, dried over MgSO₄ and concentrated in a vacuum. 12.1 g (39.3 mmol, 89%) 2-chloro-4-methyl-7-(trifluoromethyl)quinoline-3-carboxylic acid chloride was obtained as a residue. The raw product was further converted without additional purification.

c) Synthesis of 2-chloro-N-(3-fluorobenzyl)-4-methyl-7-(trifluoromethyl)quinoline-3-carboxylic acid amide A solution of 15.6 g (50.6 mmol) 2-chloro-4-methyl-7-(trifluoromethyl)quinoline-3-carboxylic acid chloride in 1,4-dioxane (85 ml) was added in drops to a solution of 7.6 g (60.8 mmol) 3-fluorobenzylamine and 10.3 ml (60.8 mmol) DIPEA in 1,4-dioxane (87 ml). The RS was subsequently stirred for 60 min at RT. The solution was then diluted with water and EA. The organic phase was separated, washed with a 4N aq. NH₄Cl sol. and brine, dried over MgSO₄ and concentrated in a vacuum. 19.4 g (48.9 mmol, 97%) 2-chloro-N-(3-fluorobenzyl)-4-methyl-7-(trifluoromethyl)quinoline-3-carboxylic acid amide was obtained as a residue. The raw product was further converted without additional purification.

d) Synthesis of 2 N-[(3-fluorophenyl)-methyl]-2-methoxy-4-methyl-7-(trifluoromethyl)-quinoline-3-carboxylic acid amide 150 mg (3.75 mmol, 60% in mineral oil) NaH was added to methanol (5 ml) and the solution was stirred for 15 min at RT. 496 mg (1.3 mmol) 2-chloro-N-(3-fluorobenzyl)-4-methyl-7-(trifluoromethyl)quinoline-3-carboxylic acid amide was then added and the RS was heated to 70° C. for 2 h. The solution was then diluted with water and EtOAc. The organic phase was separated, dried over MgSO₄ and concentrated in a vacuum. 435 mg (1.1 mmol, 89%) 2 N-[(3-fluorophenyl)-methyl]-2-methoxy-4-methyl-7-(trifluoromethyl)-quinoline-3-carboxylic acid amide (example 4) was obtained as a residue. MS: m/z 393.1 [M+H]⁺.

Synthesis of Example 5

N-[(4-fluorophenyl)-methyl]-2-methoxy-4-methyl-7-(trifluoromethyl)-quinoline-3-carboxylic acid amide a) Synthesis of 2-methoxy-4-methyl-7-(trifluoromethyl) quinoline-3-carboxylic acid A 2M aq. LiOH sol. (12 ml) was added to a solution of 1.3 g (4.0 mmol) 2-chloro-4-methyl-7-(trifluoromethyl)quinoline-3-carboxylic acid ethyl ester (synthesis see Example 3 Section a)) in a MeOH/THF mixture (in each case 10 ml) and the solution was subsequently heated to 70° C. for 16 h. The organic solvents were removed as far as possible in a vacuum and the obtained aqueous solution was washed with EtOAc, adjusted to pH 2 with 2M hydrochloric acid and diluted with EtOAc. The organic phase was separated and washed with brine, dried over MgSO₄ and concentrated in a vacuum. 754 mg (2.6 mmol, 66%) 2-methoxy-4-methyl-7-(trifluoromethyl)quinoline-3-carboxylic acid was obtained as a residue. The raw product was further converted without additional purification.

b) Synthesis of N-[(4-fluorophenyl)-methyl]-2-methoxy-4-methyl-7-(trifluoromethyl)-quinoline-3-carboxylic acid amide 87 µl (0.8 mmol) 4-fluorobenzylamine, 266 mg (0.7 mmol) HATU and 281 µl (2.0 mmol) NEt₃ were added consecutively to a solution of 199 mg (0.7 mmol) 2-methoxy-4-methyl-7-(trifluoromethyl)quinoline-3-carboxylic acid in THF (5 ml) and the solution was then stirred for 72 h at RT. The solution was subsequently diluted with EtOAc and washed with a 4N aq. NH₄Cl sol., a 1M aq. Na₂CO₃ sol. and brine. The organic phase was dried over MgSO₄, filtered through silica gel and concentrated in a vacuum. After crystallisation (EtOAc/hexane 1:2) of the residue, 161 mg (0.4 mmol, 59%) N-[(4-fluorophenyl)-methyl]-2-methoxy-4-methyl-7-(trifluoromethyl)-quinoline-3-carboxylic acid amide (example 5) was obtained. MS: m/z 393.1 [M+H]$^+$.

Synthesis of Example 7

N-[(3-fluorophenyl)-methyl]-2-(2-methoxy-ethoxy)-4-methyl-7-(trifluoromethyl)-quinoline-3-carboxylic acid amide a) Synthesis of N-(3-fluorobenzyl)-2-hydroxy-4-methyl-7-(trifluoromethyl)quinoline-3-carboxylic acid amide 508 mg (4.1 mmol) 3-fluorobenzylamine, 1.4 g (3.7 mmol) HATU and 1.5 ml (10.7 mmol) NEt$_3$ were added consecutively to a solution of 1.0 g (3.7 mmol) 2-hydroxy-4-methyl-7-(trifluoromethyl)quinoline-3-carboxylic acid (synthesis see Example 4 Section a)) in THF (28 ml) and the solution was then stirred for 16 h at 50° C. The solution was subsequently diluted with EtOAc (30 ml). The resultant precipitate was filtered off and suspended in a EtOAc/MeOH/DCM mixture. Concentration in a vacuum was subsequently carried out. 1.0 g (2.6 mmol, 71%) N-(3-fluorobenzyl)-2-hydroxy-4-methyl-7-(trifluoromethyl)quinoline-3-carboxylic acid amide was obtained as a residue. The raw product was further converted without additional purification.

b) Synthesis of N-[(3-fluorophenyl)-methyl]-2-(2-methoxy-ethoxy)-4-methyl-7-(trifluoromethyl)-quinoline-3-carboxylic acid amide 120 mg (0.9 mmol) K$_2$CO$_3$ was added to a solution of 300 mg (0.8 mmol) N-(3-fluorobenzyl)-2-hydroxy-4-methyl-7-(trifluoromethyl)quinoline-3-carboxylic acid amide in DMSO (10 ml) and the solution was stirred for 60 min at RT. 121 mg (0.9 mmol) 1-bromo-2-methoxy-ethane was then added and the RS was stirred for 16 h at RT and thereafter for 72 h at 50° C. It was then diluted with water and EtOAc. The organic phase was separated, washed with brine, dried over MgSO$_4$ and concentrated in a vacuum. After CC (EtOAc/hexane 1:3) of the residue, 72 mg (0.2 mmol, 21%) N-[(3-fluorophenyl)-methyl]-2-(2-methoxy-ethoxy)-4-methyl-7-(trifluoro-methyl)-quinoline-3-carboxylic acid amide (example 7) was obtained. MS: m/z 437.1 [M+H]$^+$.

Synthesis of Example 9

N-[(3-fluorophenyl)-methyl]-2-(2-hydroxy-ethoxy)-4-methyl-7-(trifluoromethyl)-quinoline-3-carboxylic acid amide 9.2 ml (9.2 mmol, 1M in DCM) boron tribromide was added in drops at −50° C. to a solution of 399 mg (0.9 mmol) N-[(3-fluorophenyl)-methyl]-2-(2-methoxy-ethoxy)-4-methyl-7-(trifluoro-methyl)-quinoline-3-carboxylic acid amide (Example 7) in DCM (8 ml). The mixture was subsequently heated to 0° C. within 2 h and stirred for 1 h at 0° C. The mixture was then stirred for 1 h at 10° C. It was thereafter quenched with a 0.5 M aq. NaHCO$_3$ sol. and diluted with MeOH and DCM. The organic phase was separated and washed with a 10%-strength aq. Na$_2$S$_2$O$_3$ sol., dried over MgSO$_4$ and concentrated in a vacuum. After crystallisation (EtOAc/hexane 1:1) of the residue, 109 mg (0.3 mmol, 29%) N-[(3-fluorophenyl)-methyl]-2-(2-hydroxy-ethoxy)-4-methyl-7-(trifluoromethyl)-quinoline-3-carboxylic acid amide (example 9) was obtained. MS: m/z 423.1 [M+H]$^+$.

Synthesis of Example 12

2-ethoxy-N-[(3-fluorophenyl)-methyl]-4-methoxy-7-(trifluoremethyl)-quinoline-3-carboxylic acid amide a) Synthesis of 2-ethoxy-N-(3-fluorobenzyl)-4-hydroxy-7-(trifluoromethyl)quinoline-3-carboxylic acid amide 1.5 ml (3.0 mmol, 2M in toluene)trimethylaluminium and 350 µl (3.0 mmol) 3-fluorobenzylamine were added consecutively at RT to a solution of 500 mg (1.5 mmol) 2-ethoxy-4-hydroxy-7-(trifluoromethyl)quinoline-3-carboxylic acid ethyl ester in toluene (10 ml). The RS was subsequently heated to 80° C. for 4 h. The mixture was subsequently diluted with water and extracted with EtOAc. The organic phase was washed with water and brine, dried over Na$_2$SO$_4$ and concentrated in a vacuum. After CC (EtOAc/hexane 1:9) of the residue, 250 mg (0.6 mmol, 41%) 2-ethoxy-N-(3-fluorobenzyl)-4-hydroxy-7-(trifluoromethyl)quinoline-3-carboxylic acid amide was obtained.

b) Synthesis of 2-ethoxy-N-[(3-fluorophenyl)-methyl]-4-methoxy-7-(trifluoromethyl)-quinoline-3-carboxylic acid amide 300 mg (2.2 mmol) K$_2$CO$_3$ and 0.9 ml (14.6 mmol) methyliodide were added to a solution of 300 mg (0.7 mmol) 2-ethoxy-N-(3-fluorobenzyl)-4-hydroxy-7-(trifluoro-methyl)quinoline-3-carboxylic acid amide in DMF (5 ml) and the mixture was stirred for 16 h at RT. The mixture was subsequently diluted with water and extracted with EtOAc. The organic phase was washed with water and brine, dried over Na$_2$SO$_4$ and concentrated in a vacuum. After CC (EtOAc/hexane 1:12) of the residue, 240 mg (0.6 mmol, 81%) 2-ethoxy-N-[(3-fluorophenyl)-methyl]-4-methoxy-7-(trifluoromethyl)-quinoline-3-carboxylic acid amide (example 12) was obtained. MS: m/z 423.1 [M+H]$^+$.

Synthesis of Example 13

N-[(3-fluorophenyl)-methyl]-2,4-dimethoxy-7-(trifluoromethyl)-quinoline-3-carboxylic acid amide a) Synthesis of N-(3-fluorobenzyl)-2,4-dihydroxy-7-(trifluoromethyl)quinoline-3-carboxylic acid amide 2.0 ml (17.3 mmol) 3-fluorobenzylamine was added to a suspension of 1.3 g (4.3 mmol) 2,4-dihydroxy-7-(trifluoromethyl)quinoline-3-carboxylic acid ethyl ester in EtOH (50 ml) and the mixture was heated to 90° C. for 3 h. Concentration in a vacuum was subsequently carried out. After CC (DCM) of the residue, 1.6 g (4.2 mmol, 98%) N-(3-fluorobenzyl)-2,4-dihydroxy-7-(trifluoromethyl)quinoline-3-carboxylic acid amide was obtained.

b) Synthesis of N-[(3-fluorophenyl)-methyl]-2,4-dimethoxy-7-(trifluoromethyl)-quinoline-3-carboxylic acid amide 1.8 g (6.6 mmol) Ag$_2$CO$_3$ was added to a solution of 500 mg (1.3 mmol) N-(3-fluorobenzyl)-2,4-dihydroxy-7-(trifluoromethyl)-quinoline-3-carboxylic acid in DCM (15 ml) and the solution was stirred for 10 min at RT. 820 µl (13.2 mmol) methyliodide was then added and the RS was stirred for a further 20 h at RT. Filtering off was then performed and the filtrate was concentrated in a vacuum. After CC (EtOAc/hexane 1:12) of the residue, 51 mg (0.1 mmol, 9%) N-[(3-fluorophenyl)-methyl]-2,4-dimethoxy-7-(trifluoromethyl)-quinoline-3-carboxylic acid amide (example 13) was obtained. MS: m/z 409.1 [M+H]$^+$.

Synthesis of Example 36

7-Cyano-2-ethoxy-N-[(3-fluorophenyl)-methyl]-4-methyl-quinoline-3-carboxylic acid amide To a solution of 600 mg (1.44 mmol) 7-bromo-2-ethoxy-N-[(3-fluorophenyl)-methyl]-4-methyl-quinoline-3-carboxylic acid amide (example 32) in DMF (3 mL) were added 46 µL (0.32 mmol) TMEDA, 102 mg (0.86 mmol) zinc cyanide, 2 mg (0.007 mmol) $Pd_2 dba_3$ and Xantphos. The reaction solution was degasses and flushed with nitrogen three times and then heated in MW to 160° C. for 4 min. After cooling to RT the mixture was filtered through celite and it was washed with dichloromethane. The combined organic layers were concentrated in vacuo. After CC (EtOAc/hexane 1:2) of the residue, 310 mg (0.85 mmol, 59%) 7-Cyano-2-ethoxy-N-[(3-fluorophenyl)-methyl]-4-methyl-quinoline-3-carboxylic acid amide (example 36) were obtained. MS: m/z 364.1 $[M+H]^+$.

Synthesis of Example 42

N-[(3-Fluoro-2-hydroxy-phenyl)-methyl]-2-methoxy-4-methyl-7-(trifluoromethyl)-quinoline-3-carboxylic acid amide a) Synthesis of N-[(3-Fluoro-2-methoxy-phenyl)-methyl]-2-chloro-4-methyl-7-(trifluoromethyl)-quinoline-3-carboxylic acid amide The synthesis was performed analogous to the synthesis described for example 4 section c)

b) Synthesis of N-[(3-Fluoro-2-hydroxy-phenyl)-methyl]-2-chloro-4-methyl-7-(trifluoromethyl)-quinoline-3-carboxylic acid amide A solution of 278 mg (0.65 mmol) N-[(3-fluoro-2-methoxy-phenyl)-methyl]-2-chloro-4-methyl-7-(trifluoromethyl)-quinoline-3-carboxylic acid amide in DCM (13 ml) was cooled to −30° C. and subsequently treated with 6.5 ml (6.5 mmol, 1M in DCM) tribromoborane at this temperature. After stirring at −5° C. for 3 h, the reaction mixture was stirred at 0° C. for 16 h, followed by quenching with a 1M aq, $NaHCO_3$ sol. The layers were separated and the aqueous layer was extracted with EtOAc. The combined organic layers were dried washed brine, dried over $MgSO_4$. After filtering and concentration in vacuum 241 mg (0.56 mmol, 87%) N-[(3-Fluoro-2-hydroxy-phenyl)-methyl]-2-chloro-4-methyl-7-(trifluoromethyl)-quinoline-3-carboxylic acid amide were obtained.

c) Synthesis of N-[(3-Fluoro-2-hydroxy-phenyl)-methyl]-2-methoxy-4-methyl-7-(trifluoromethyl)-quinoline-3-carboxylic acid amide Reaction of 238 mg (0.57 mmol) N-[(3-fluoro-2-hydroxy-phenyl)-methyl]-2-chloro-4-methyl-7-(trifluoromethyl)-quinoline-3-carboxylic acid amide following the procedure as described for example 4 section d) provided 45 mg (0.11 mmol, 19%) N-[(3-Fluoro-2-hydroxy-phenyl)-methyl]-2-methoxy-4-methyl-7-(trifluoromethyl)-quinoline-3-carboxylic acid amide (example 42). MS: m/z 409.1 $[M+H]^+$.

Synthesis of Example 46

N-[(3-Fluoro-2-hydroxy-phenyl)-methyl]-2-methoxy-4-methyl-7-(trifluoromethyl)-quinoline-3-carboxylic acid amide a) Synthesis of 7-fluoro-2-hydroxy-4-methylquinoline-3-carboxylic acid ethyl ester The synthesis was performed analogous to the synthesis described for example 2 section a)

b) Synthesis of 7-fluoro-2-methoxy-4-methylquinoline-3-carboxylic acid ethyl ester To a stirred solution of 2.30 g (9.24 mmol) 7-fluoro-2-hydroxy-4-methylquinoline-3-carboxylic acid ethyl ester in DCM (60 ml) were added 6.36 g (23.1 mmol) $Ag_2CO_3$ and 1.44 ml (23.1 mmol) iodomethane at RT. The reaction mixture was stirred at RT for 16 h. Then the mixture was filtered through celite and the filtrate was concentrated in vacuum. After CC (EtOAc/hexane 1:4) of the residue, 1.50 g (5.70 mmol, 62%) 7-fluoro-2-methoxy-4-methylquinoline-3-carboxylic acid ethyl ester were obtained.

c) Synthesis of 7-Fluoro-N-[(4-fluorophenyl)-methyl]-2-methoxy-4-methyl-quinoline-3-carboxylic acid amide To a stirred solution of 400 mg (1.52 mmol) 7-fluoro-2-methoxy-4-methylquinoline-3-carboxylic acid ethyl ester in toluene (10 ml) were added 3.04 ml (2M solution in toluene, 6.1 mmol) $Me_3Al$ at RT followed by the addition of 700 µl (6.1 mmol) 4-fluorobenzylamine. The reaction mixture was heated at 110° C. for 16 h. Then the reaction was quenched with water (10 ml) and extracted with EtOAc (3×20 ml). The combined organic layers were washed with water (20 ml), brine (20 ml), dried over $Na_2SO_4$ and concentrated in vacuum. After CC (EtOAc/hexane 1:4) of the residue, 160 mg (0.47 mmol, 31%) 7-fluoro-N-[(4-fluorophenyl)-methyl]-2-methoxy-4-methyl-quinoline-3-carboxylic acid amide (example 46) were obtained. MS: m/z 343.1 $[M+H]^+$.

Synthesis of Further Examples

The synthesis of further examples was carried out according to the methods already described. Table 1 shows which compound was produced according to which method. It is evident to the person skilled in the art which educts and reagents were used in each case.

TABLE 1

| Example | chemical name | Preparation analogous to example | MS m/z $[M + H]^+$ |
|---|---|---|---|
| 1 | N-(3,3-Dimethyl-butyl)-2-methoxy-4-methyl-7-(trifluoromethyl)-quinoline-3-carboxylic acid amide | 3 | 369.2 |
| 6 | 2-Ethoxy-N-[(3-fluorophenyl)-methyl]-4-methyl-7-(trifluoromethyl)-quinoline-3-carboxylic acid amide | 3 | 407.1 |
| 8 | N-[(4-Fluorophenyl)-methyl]-2-(2-methoxy-ethoxy)-4-methyl-7-(trifluoromethyl)-quinoline-3-carboxylic acid amide | 7 | 437.1 |

TABLE 1-continued

| Example | chemical name | Preparation analogous to example | MS m/z [M + H]+ |
|---|---|---|---|
| 10 | N-[(3-Fluorophenyl)-methyl]-2-isopropoxy-4-methyl-7-(trifluoromethyl)-quinoline-3-carboxylic acid amide | 4 | 421.1 |
| 11 | N-[(4-Fluorophenyl)-methyl]-2-isopropoxy-4-methyl-7-(trifluoromethyl)-quinoline-3-carboxylic acid amide | 4 | 421.1 |
| 14 | 2-Ethoxy-N-[(4-fluorophenyl)-methyl]-4-methoxy-7-(trifluoromethyl)-quinoline-3-carboxylic acid amide | 12 | 423.1 |
| 15 | 2-Ethoxy-6,7-difluoro-N-[(3-fluorophenyl)-methyl]-4-methoxy-quinoline-3-carboxylic acid amide | 12 | 391.1 |
| 16 | N-[(4-Fluorophenyl)-methyl]-2,4-dimethoxy-7-(trifluoromethyl)-quinoline-3-carboxylic acid amide | 13 | 409.1 |
| 17 | 6,7-Difluoro-N-[(3-fluorophenyl)-methyl]-2,4-dimethoxy-quinoline-3-carboxylic acid amide | 13 | 377.1 |
| 18 | 7-Fluoro-N-[(3-fluorophenyl)-methyl]-2-methoxy-4-methyl-quinoline-3-carboxylic acid amide | 2 | 343.1 |
| 19 | N-[(3-Fluoro-4-methyl-phenyl)-methyl]-2-methoxy-4-methyl-7-(trifluoromethyl)-quinoline-3-carboxylic acid amide | 3 | 407.1 |
| 20 | 2-Ethoxy-N-[(3-fluoro-4-methyl-phenyl)-methyl]-4-methyl-7-(trifluoromethyl)-quinoline-3-carboxylic acid amide | 3 | 421.1 |
| 21 | 2-Methoxy-4-methyl-N-(m-tolyl-methyl)-7-(trifluoromethyl)-quinoline-3-carboxylic acid amide | 3 | 389.1 |
| 22 | 2-Ethoxy-4-methyl-N-(m-tolyl-methyl)-7-(trifluoromethyl)-quinoline-3-carboxylic acid amide | 3 | 403.2 |
| 23 | N-[(4-Fluoro-3-methyl-phenyl)-methyl]-2-methoxy-4-methyl-7-(trifluoromethyl)-quinoline-3-carboxylic acid amide | 3 | 407.1 |
| 24 | 2-Ethoxy-N-[(4-fluoro-3-methyl-phenyl)-methyl]-4-methyl-7-(trifluoromethyl)-quinoline-3-carboxylic acid amide | 3 | 421.1 |
| 25 | 2-Methoxy-4-methyl-N-(p-tolyl-methyl)-7-(trifluoromethyl)-quinoline-3-carboxylic acid amide | 3 | 389.1 |
| 26 | 2-Ethoxy-4-methyl-N-(p-tolyl-methyl)-7-(trifluoromethyl)-quinoline-3-carboxylic acid amide | 3 | 403.2 |
| 27 | 2-Ethoxy-4-methyl-N-(4-methyl-pentyl)-7-(trifluoromethyl)-quinoline-3-carboxylic acid amide | 3 | 383.2 |
| 28 | 2-Methoxy-4-methyl-N-(4-methyl-pentyl)-7-(trifluoromethyl)-quinoline-3-carboxylic acid amide | 3 | 369.2 |
| 29 | N-(4,4-Dimethyl-pentyl)-2-methoxy-4-methyl-7-(trifluoromethyl)-quinoline-3-carboxylic acid amide | 3 | 383.2 |
| 30 | N-(4,4-Dimethyl-pentyl)-2-ethoxy-4-methyl-7-(trifluoromethyl)-quinoline-3-carboxylic acid amide | 3 | 397.2 |
| 31 | 7-Bromo-2-ethoxy-N-[(4-fluorophenyl)-methyl]-4-methyl-quinoline-3-carboxylic acid amide | 3 | 417.1 |
| 32 | 7-Bromo-2-ethoxy-N-[(3-fluorophenyl)-methyl]-4-methyl-quinoline-3-carboxylic acid amide | 3 | 417.1 |
| 33 | 7-Bromo-N-[(3-fluorophenyl)-methyl]-2-methoxy-4-methyl-quinoline-3-carboxylic acid amide | 3 | 403.0 |
| 34 | 7-Bromo-N-[(4-fluorophenyl)-methyl]-2-methoxy-4-methyl-quinoline-3-carboxylic acid amide | 3 | 403.0 |
| 35 | 7-Cyano-2-ethoxy-N-[(4-fluorophenyl)-methyl]-4-methyl-quinoline-3-carboxylic acid amide | 36 | 364.1 |
| 37 | 7-Cyano-N-[(3-fluorophenyl)-methyl]-2-methoxy-4-methyl-quinoline-3-carboxylic acid amide | 36 | 350.1 |
| 38 | 7-Cyano-N-[(4-fluorophenyl)-methyl]-2-methoxy-4-methyl-quinoline-3-carboxylic acid amide | 36 | 350.1 |

TABLE 1-continued

| Example | chemical name | Preparation analogous to example | MS m/z [M + H]+ |
|---|---|---|---|
| 39 | N-[(3-Fluoro-2-methoxy-phenyl)-methyl]-2-methoxy-4-methyl-7-(trifluoromethyl)-quinoline-3-carboxylic acid amide | 3 | 423.1 |
| 40 | N-[(3-Fluoro-5-methoxy-phenyl)-methyl]-2-methoxy-4-methyl-7-(trifluoromethyl)-quinoline-3-carboxylic acid amide | 3 | 423.1 |
| 41 | N-[(5-Fluoro-2-methoxy-phenyl)-methyl]-2-methoxy-4-methyl-7-(trifluoromethyl)-quinoline-3-carboxylic acid amide | 3 | 423.1 |
| 43 | N-[(3-Fluoro-5-hydroxy-phenyl)-methyl]-2-methoxy-4-methyl-7-(trifluoromethyl)-quinoline-3-carboxylic acid amide | 42 | 409.1 |
| 44 | N-[(5-Fluoro-2-hydroxy-phenyl)-methyl]-2-methoxy-4-methyl-7-(trifluoromethyl)-quinoline-3-carboxylic acid amide | 42 | 409.1 |
| 45 | N-[(3-Fluoro-4-hydroxy-phenyl)-methyl]-2-methoxy-4-methyl-7-(trifluoromethyl)-quinoline-3-carboxylic acid amide | 42 | 409.1 |
| 47 | 5,7-Difluoro-N-[(3-fluorophenyl)-methyl]-2-methoxy-4-methyl-quinoline-3-carboxylic acid amide | 46 | 361.1 |
| 48 | 6,7-Difluoro-N-[(3-fluorophenyl)-methyl]-2-methoxy-4-methyl-quinoline-3-carboxylic acid amide | 46 | 361.1 |
| 49 | 7,8-Difluoro-N-[(3-fluorophenyl)-methyl]-2-methoxy-4-methyl-quinoline-3-carboxylic acid amide | 46 | 361.1 |
| 50 | N-[(3-Fluorophenyl)-methyl]-4-methyl-2-(2,2,2-trifluoro-ethoxy)-7-(trifluoromethyl)-quinoline-3-carboxylic acid amide | 4 | 461.1 |
| 51 | N-[(3-Fluorophenyl)-methyl]-2-methoxy-4-(trifluoromethyl)-quinoline-3-carboxylic acid amide | 4 | 379.1 |
| 52 | 2-Ethoxy-N-[(3-fluorophenyl)-methyl]-4-(trifluoromethyl)-quinoline-3-carboxylic acid amide | 4 | 393.1 |
| 53 | N-[(3-Fluorophenyl)-methyl]-2-isopropoxy-4-(trifluoromethyl)-quinoline-3-carboxylic acid amide | 4 | 407.1 |

Pharmacological Experiments
Method I. Fluorescence Assay Using a Voltage Sensitive Dye (Fluorimetry)

Human CHO-K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% fetal calf serum (FCS) (Invitrogen, #10270-106, heat-inactivated) and the necessary selection antibiotics.

Before being sown out for the measurements, the cells are washed with 1×DPBS buffer $Ca^{2+}/Mg^{2+}$-free (e.g. Invitrogen, #14190-094) and detached from the bottom of the culture vessel by using Accutase (PAA Laboratories, #L11-007) (incubation with Accutase for 15 min at 37° C.). The cell number is determined using a CASY™ cell counter (TCC, Schärfe System). Depending on the optimal density for each individual cell line, 20,000-30,000 cells/well/100 µl are seeded onto 96-well Corning™ CellBIND™ assay plates (Flat Clear Bottom Black Polystyrene Microplates, #3340). Freshly seeded cells are then left to settle for one hour at room temperature, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of one vessel *Membrane Potential Assay Kit Red Component A* in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed once with 200 µl of ES buffer, then loaded for 45 min at room temperature in 100 µl of dye solution in the dark.

Fluorescence measurements are carried out in a BMG Labtech FLUOstar™, BMG Labtech NOVOstar™ or BMG Labtech POLARstar™ instrument (525 nm excitation, 560 nm emission, Bottom Read mode). After incubation with the dye, 50 µl of the test substances in the desired concentrations, or 50 µl of ES buffer for control purposes, are applied to the wells of the assay plate and incubated for 30 min at room temperature while being shielded from light. The fluorescence intensity of the dye is then measured for 5 min and the fluorescence value $F_1$ of each well is thus determined at a given, constant time. 15 µl of a KCl solution are then added to each well (final concentration of potassium ions 92 mM). The change in fluorescence intensity is subsequently monitored until all the relevant values have been obtained (mainly 5-30 min). At a given time post KCl application, a fluorescence value $F_2$ is determined, in this case at the time of the fluorescence peak.

For calculation, the fluorescence intensity $F_2$ is corrected for the fluorescence intensity $F_1$, and the activity ($\Delta F/F$) of the target compound on the potassium channel is determined as follows:

$$\left(\frac{F_2 - F_1}{F_1}\right) \times 100 = \frac{\Delta F}{F}(\%)$$

In order to determine whether a substance has agonistic activity $$\frac{\Delta F}{F}$$

can be related to $$\left(\frac{\Delta F}{F}\right)_K$$

of control wells.

$$\left(\frac{\Delta F}{F}\right)_K$$

is determined by adding to the well only the buffer solution instead of the test substance, determining the value $F_{1K}$ of the fluorescence intensity, adding the potassium ions as described above, and measuring a value $F_{2K}$ of the fluorescence intensity. $F_{2K}$ and $F_{1K}$ are then calculated as follows:

$$\left(\frac{F_{2K} - F_{1K}}{F_{1K}}\right) \times 100 = \left(\frac{\Delta F}{F}\right)_K (\%)$$

A substance has an agonistic activity on the potassium channel if $$\frac{\Delta F}{F}$$

is greater than $$\left(\frac{\Delta F}{F}\right)_K:$$

$$\frac{\Delta F}{F}\bigg)\left(\frac{\Delta F}{F}\right)_K$$

Independently of the comparison of $$\frac{\Delta F}{F}$$

with $$\left(\frac{\Delta F}{F}\right)_K$$

it is possible to conclude that a target compound has agonistic activity if $$\frac{\Delta F}{F}$$

increases dose dependently.

Calculations of $EC_{50}$ and $IC_{50}$ values are carried out with the aid of "Prism v4.0" software (GraphPad Software™)

Method II. Low-Intensity Tail Flick Test (Rat)

In the low-intensity tail flick test, the determination of the antinociceptive effect of the compounds according to the invention towards an acute noxious thermal stimulus is carried out by measuring the withdrawal reflex of the rat tail (tail flick) in response to a radiant heat beam (analgesia meter; model 2011 of the company Rhema Labortechnik, Hofheim, Germany) according to the method described by D'Annour and Smith (J. Pharm. Exp. Ther. 72, 74 79 (1941). To this end, the rats were placed in a plexiglas restrainer, and a low-intensity radiant heat beam (48° C.) was focused onto the dorsal surface of the tail root. The stimulus intensity was adjusted to result in a mean pre-drug control withdrawal latency of about 7 s, thus also allowing a supraspinal modulation of the spinally mediated acute nociceptive reflex. A cutoff time of 30 s was applied to avoid tissue damage. Male Sprague-Dawley rats (Janvier, Le Genest St. Isle, Frankreich) with weights of 200-250 g were used. 10 rats were used per group. Before administration of a compound according to the invention, the animals were pre-tested twice in the course of five minutes and the mean of these measurements was calculated as the pre-test mean. The antinociceptive effect was determined at 20, 40 and 60 min after peroral compound administration. The antinociceptive effect was calculated based on the increase in the tail withdrawal latency according to the following formula and is expressed as percentage of the maximum possible effect (MPE [%]):

$$MPE=[(T_1-T_0)/(T_2-T_0)]*100$$

In this, $T_0$ is the control latency time before and $T_1$ the latency time after administration of the compound, $T_2$ is the cutoff time and MPE is the maximum possible effect. Employing variant analysis (repeated measures ANOVA) allowed testing of statistically significant differences between the compounds according to the invention and the vehicle group. The significance level was set to $p \leq 0.05$. To determine the dose dependency, the particular compound according to the invention was administered in 3-5 logarithmically increasing doses, including a threshold dose and a maximum effective dose, and the $ED_{50}$ values were determined with the aid of regression analysis. The $ED_{50}$ calculation was performed at the time of maximum efficacy (usually 20 min after administration of the compounds).

Pharmacological Data

The pharmacological effects of the compounds according to the invention were determined as described hereinbefore (pharmacological experiments, methods I and II respectively).

The corresponding pharmacological data are summarized in Table 2.

TABLE 2

| Example | Fluorimetry % efficacy (retigabine = 100%) | Fluorimetry $EC_{50}$ [nM] | Low intensity tail flick, rat, peroral, $ED_{50}$ or MPE (dose) [mg/kg] |
|---|---|---|---|
| 1 | 57 | | |
| 2 | 175 | 64 | |
| 3 | 122 | 39 | 2.5 |
| 4 | 105 | 73 | 6.7 |
| 5 | 122 | 57 | 34% (6.81) |
| 6 | 132 | 58 | 67% (4.64) |
| 7 | 92 | 96 | 10.0 |
| 8 | 94 | 143 | 22% (10.00) |
| 9 | 119 | 390 | |
| 10 | 175 | 87 | 3.8 |
| 11 | 164 | 52 | |
| 12 | 170 | 104 | 27% (4.64) |
| 13 | 147 | 136 | 10% (10.00) |
| 14 | 155 | 75 | |
| 15 | 181 | 106 | |
| 16 | 159 | 106 | 74% (10.00) |
| 17 | 147 | 218 | |
| 18 | 62 | 340 | |
| 19 | 99 | 92 | |
| 20 | 146 | 72 | 24% (10.00) |
| 21 | 71 | 67 | |
| 22 | 111 | 58 | 20% (10.00) |
| 23 | 73 | 62 | |
| 24 | 108 | 53 | 17% (6.81) |
| 25 | 96 | 182 | |
| 26 | 117 | 131 | |
| 27 | 173 | 84 | |
| 28 | 184 | 81 | |
| 29 | 244 | 28 | 28% (10.00) |
| 30 | 214 | 50 | |
| 35 | 112 | 82 | 32% (6.81) |
| 36 | 105 | 56 | |
| 37 | 85 | 261 | |
| 38 | 74 | 143 | |
| 39 | 10 | | |
| 40 | 15 | | |
| 41 | 140 | 1541 | |
| 42 | 137 | 123 | |
| 43 | 9 | | |
| 44 | 173 | 79 | |
| 45 | 87 | 2057 | |
| 46 | 59 | 299 | |
| 47 | 43 | | |
| 48 | 96 | 315 | |
| 49 | 70 | 229 | |
| 50 | 108 | 25 | 24% @ 10.00 |
| 51 | 40 | | |
| 52 | 67 | 205 | |
| 53 | 84 | 108 | |

The invention claimed is:

1. A substituted compound of the formula:

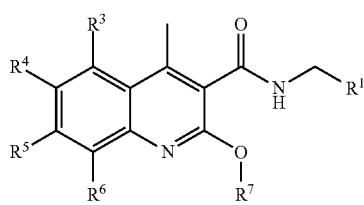

wherein
$R^1$ represents the partial structure (T1),

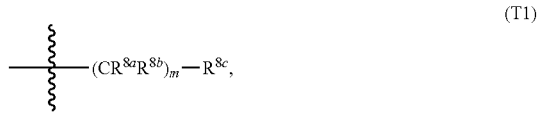

wherein
m is 0, 1 or 2 and
$R^{8a}$ and $R^{8b}$ each independently of one another represent H, F, a O—$C_{1-4}$ aliphatic residue or a $C_{1-4}$ aliphatic residue;
$R^{8c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or
wherein
m is 0,
$R^{8c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl,
wherein phenyl may be unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)-$CH_3$, C(=O)—$C_2H_5$, C(=O)—O—$CH_3$ and C(=O)—O—$C_2H_5$,
$R^3$, $R^4$, $R^5$ and $R^6$ are each independently of one another selected from the group consisting of H; F; Cl; Br; $CF_3$; CN; $OCF_3$ and $NO_2$; and
$R^7$ denotes methyl or ethyl;
said compound being in the form of a free compound, a racemic mixture, an individual enantiomer, an individual diastereomer, a mixture of enantiomers or diastereomers or diastereomers in any mixing ratio, or in the form of a salt of a physiologically acceptable acid or base.

2. The compound according to claim 1, wherein the compound is selected from the group consisting of:
1 N-(3,3-dimethyl-butyl)-2-methoxy-4-methyl-7-(trifluoromethyl)-quinoline-3-carboxylic acid amide;
2 2-ethoxy-4-methyl-N-(thiophene-2-yl-methyl)-7-(trifluoromethyl)-quinoline-3-carboxylic acid amide;
3 2-ethoxy-N-[(4-fluorophenyl)-methyl]-4-methyl-7-(trifluoromethyl)-quinoline-3-carboxylic acid amide;
4 N-[(3-fluorophenyl)-methyl]-2-methoxy-4-methyl-7-(trifluoromethyl)-quinoline-3-carboxylic acid amide;
5 N-[(4-fluorophenyl)-methyl]-2-methoxy-4-methyl-7-(trifluoromethyl)-quinoline-3-carboxylic acid amide;

6 2-ethoxy-N-[(3-fluorophenyl)-methyl]-4-methyl-7-(trifluoromethyl)-quinoline-3-carboxylic acid amide;
18 7-fluoro-N-[(3-fluorophenyl)-methyl]-2-methoxy-4-methyl-quinoline-3-carboxylic acid amide;
19 N-[(3-fluoro-4-methyl-phenyl)-methyl]-2-methoxy-4-methyl-7-(trifluoromethyl)-quinoline-3-carboxylic acid amide;
20 2-ethoxy-N-[(3-fluoro-4-methyl-phenyl)-methyl]-4-methyl-7-(trifluoromethyl)-quinoline-3-carboxylic acid amide;
21 2-methoxy-4-methyl-N-(m-tolyl-methyl)-7-(trifluoromethyl)-quinoline-3-carboxylic acid amide;
22 2-ethoxy-4-methyl-N-(m-tolyl-methyl)-7-(trifluoromethyl)-quinoline-3-carboxylic acid amide;
23 N-[(4-fluoro-3-methyl-phenyl)-methyl]-2-methoxy-4-methyl-7-(trifluoromethyl)-quinoline-3-carboxylic acid amide;
24 2-ethoxy-N-[(4-fluoro-3-methyl-phenyl)-methyl]-4-methyl-7-(trifluoromethyl)-quinoline-3-carboxylic acid amide;
25 2-methoxy-4-methyl-N-(p-tolyl-methyl)-7-(trifluoromethyl)-quinoline-3-carboxylic acid amide;
26 2-ethoxy-4-methyl-N-(p-tolyl-methyl)-7-(trifluoromethyl)-quinoline-3-carboxylic acid amide;
27 2-ethoxy-4-methyl-N-(4-methyl-pentyl)-7-(trifluoromethyl)-quinoline-3-carboxylic acid amide;
28 2-methoxy-4-methyl-N-(4-methyl-pentyl)-7-(trifluoromethyl)-quinoline-3-carboxylic acid amide;
29 N-(4,4-dimethyl-pentyl)-2-methoxy-4-methyl-7-(trifluoromethyl)-quinoline-3-carboxylic acid amide;
30 N-(4,4-dimethyl-pentyl)-2-ethoxy-4-methyl-7-(trifluoromethyl)-quinoline-3-carboxylic acid amide;
31 7-bromo-2-ethoxy-N-[(4-fluorophenyl)-methyl]-4-methyl-quinoline-3-carboxylic acid amide;
32 7-bromo-2-ethoxy-N-[(3-fluorophenyl)-methyl]-4-methyl-quinoline-3-carboxylic acid amide;
33 7-bromo-N-[(3-fluorophenyl)-methyl]-2-methoxy-4-methyl-quinoline-3-carboxylic acid amide;
34 7-bromo-N-[(4-fluorophenyl)-methyl]-2-methoxy-4-methyl-quinoline-3-carboxylic acid amide;
35 7-cyano-2-ethoxy-N-[(4-fluorophenyl)-methyl]-4-methyl-quinoline-3-carboxylic acid amide;
36 7-cyano-2-ethoxy-N-[(3-fluorophenyl)-methyl]-4-methyl-quinoline-3-carboxylic acid amide;
37 7-cyano-N-[(3-fluorophenyl)-methyl]-2-methoxy-4-methyl-quinoline-3-carboxylic acid amide;
38 7-cyano-N-[(4-fluorophenyl)-methyl]-2-methoxy-4-methyl-quinoline-3-carboxylic acid amide;
39 N-[(3-fluoro-2-methoxy-phenyl)-methyl]-2-methoxy-4-methyl-7-(trifluoromethyl)-quinoline-3-carboxylic acid amide;
40 N-[(3-fluoro-5-methoxy-phenyl)-methyl]-2-methoxy-4-methyl-7-(trifluoromethyl)-quinoline-3-carboxylic acid amide;
41 N-[(5-fluoro-2-methoxy-phenyl)-methyl]-2-methoxy-4-methyl-7-(trifluoromethyl)-quinoline-3-carboxylic acid amide;
42 N-[(3-fluoro-2-hydroxy-phenyl)-methyl]-2-methoxy-4-methyl-7-(trifluoromethyl)-quinoline-3-carboxylic acid amide;
43 N-[(3-fluoro-5-hydroxy-phenyl)-methyl]-2-methoxy-4-methyl-7-(trifluoromethyl)-quinoline-3-carboxylic acid amide;
44 N-[(5-fluoro-2-hydroxy-phenyl)-methyl]-2-methoxy-4-methyl-7-(trifluoromethyl)-quinoline-3-carboxylic acid amide;
45 N-[(3-fluoro-4-hydroxy-phenyl)-methyl]-2-methoxy-4-methyl-7-(trifluoromethyl)-quinoline-3-carboxylic acid amide;
46 7-fluoro-N-[(4-fluorophenyl)-methyl]-2-methoxy-4-methyl-quinoline-3-carboxylic acid amide:
47 5,7-difluoro-N-[(3-fluorophenyl)-methyl]-2-methoxy-4-methyl-quinoline-3-carboxylic acid amide;
48 6,7-difluoro-N-[(3-fluorophenyl)-methyl]-2-methoxy-4-methyl-quinoline-3-carboxylic acid amide; and
49 7,8-difluoro-N-[(3-fluorophenyl)-methyl]-2-methoxy-4-methyl-quinoline-3-carboxylic acid amide;

said compound being in the form of a free compound, a racemic mixture, an individual enantiomer, an individual diastereomer, a mixture of enantiomers or diastereomers or diastereomers in any mixing ratio, or in the form of a salt of a physiologically acceptable acid or base.

3. A pharmaceutical composition comprising at least one compound according to claim 1 and optionally at least one pharmaceutically acceptable auxiliary and/or optionally at least one further active ingredient.

4. A method for the treatment of a disorder and/or disease in a mammal in need thereof, wherein said disorder and/or disease is mediated, at least in part, by KCNQ2/3 $K^+$ channels, and wherein said disorder and/or disease is selected from the group consisting of pain, epilepsy, urinary incontinence, anxiety, dependency, mania, bipolar disorders, migraine, and dystonia-associated dyskinesias, said method comprising administering an effective amount therefor of at least one compound according to claim 1 to the mammal.

5. The compound according to claim 1, which is 2-ethoxy-N-[(4-fluorophenyl)-methyl]-4-methyl-7-(trifluoromethyl)-quinoline-3-carboxylic acid amide, having the formula:

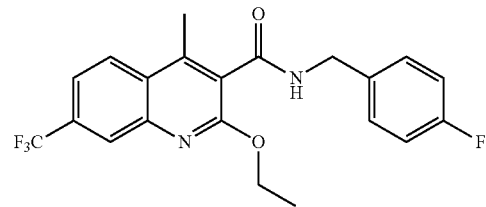 [SMILES: CCOc1nc2cc(C(F)(F)F)ccc2c(C)c1C(=O)NCc1ccc(F)cc1]

said compound being in the form of a free compound, a racemic mixture, an individual enantiomer, an individual diastereomer, a mixture of enantiomers or diastereomers or diastereomers in any mixing ratio, or in the form of a salt of a physiologically acceptable acid or base.

6. The compound according to claim 1, which is N-[(3-fluorophenyl)-methyl]-2-methoxy-4-methyl-7-(trifluoromethyl)-quinoline-3-carboxylic acid amide, having the formula:

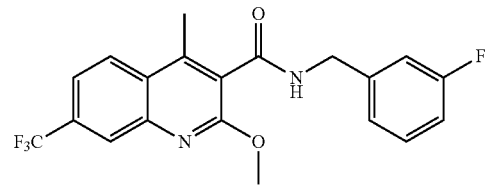 [SMILES: COc1nc2cc(C(F)(F)F)ccc2c(C)c1C(=O)NCc1cccc(F)c1]

said compound being in the form of a free compound, a racemic mixture, an individual enantiomer, an individual diastereomer, a mixture of enantiomers or diastereomers or diastereomers in any mixing ratio, or in the form of a salt of a physiologically acceptable acid or base.

7. The compound according to claim 1, which is 2-ethoxy-N-[(3-fluorophenyl)-methyl]-4-methyl-7-(trifluoromethyl)-quinoline-3-carboxylic acid amide, having the formula:

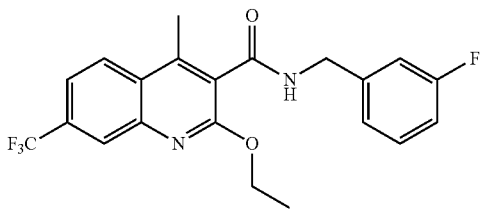 [SMILES: CCOc1nc2cc(C(F)(F)F)ccc2c(C)c1C(=O)NCc1cccc(F)c1]

said compound being in the form of a free compound, a racemic mixture, an individual enantiomer, an individual diastereomer, a mixture of enantiomers or diastereomers or diastereomers in any mixing ratio, or in the form of a salt of a physiologically acceptable acid or base.

8. The compound according to claim 1, which is 7-cyano-2-ethoxy-N-[(4-fluorophenyl)-methyl]-4-methyl-quinoline-3-carboxylic acid amide, having the formula:

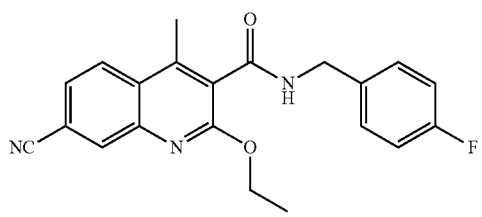 [SMILES: CCOc1nc2cc(C#N)ccc2c(C)c1C(=O)NCc1ccc(F)cc1]

said compound being in the form of a free compound, a racemic mixture, an individual enantiomer, an individual diastereomer, a mixture of enantiomers or diastereomers or diastereomers in any mixing ratio, or in the form of a salt of a physiologically acceptable acid or base.

9. A pharmaceutical composition comprising at least one compound according to claim 5 and optionally at least one pharmaceutically acceptable auxiliary and/or optionally at least one further active ingredient.

10. A pharmaceutical composition comprising at least one compound according to claim 6 and optionally at least one pharmaceutically acceptable auxiliary and/or optionally at least one further active ingredient.

11. A pharmaceutical composition comprising at least one compound according to claim 7 and optionally at least one pharmaceutically acceptable auxiliary and/or optionally at least one further active ingredient.

12. A pharmaceutical composition comprising at least one compound according to claim 8 and optionally at least one pharmaceutically acceptable auxiliary and/or optionally at least one further active ingredient.

13. A method for the treatment of a disorder and/or disease in a mammal in need thereof, wherein said disorder and/or disease is mediated, at least in part, by KCNQ2/3 $K^+$ channels, and wherein said disorder and/or disease is selected from the group consisting of pain, epilepsy, urinary incontinence, anxiety, dependency, mania, bipolar disorders, migraine, and dystonia-associated dyskinesias, said method comprising administering an effective amount therefor of at least one compound according to claim 5 to the mammal.

14. A method for the treatment of a disorder and/or disease in a mammal in need thereof, wherein said disorder and/or disease is mediated, at least in part, by KCNQ2/3 $K^+$ channels, and wherein said disorder and/or disease is selected from the group consisting of pain, epilepsy, urinary incontinence, anxiety, dependency, mania, bipolar disorders, migraine, and dystonia-associated dyskinesias, said method comprising administering an effective amount therefor of at least one compound according to claim 6 to the mammal.

15. A method for the treatment of a disorder and/or disease in a mammal in need thereof, wherein said disorder and/or disease is mediated, at least in part, by KCNQ2/3 $K^+$ channels, and wherein said disorder and/or disease is selected from the group consisting of pain, epilepsy, urinary incontinence, anxiety, dependency, mania, bipolar disorders, migraine, and dystonia-associated dyskinesias, said method comprising administering an effective amount therefor of at least one compound according to claim 7 to the mammal.

16. A method for the treatment of a disorder and/or disease in a mammal in need thereof, wherein said disorder and/or disease is mediated, at least in part, by KCNQ2/3 $K^{30}$ channels, and wherein said disorder and/or disease is selected from the group consisting of pain, epilepsy, urinary incontinence, anxiety, dependency, mania, bipolar disorders, migraine, and dystonia-associated dyskinesias, said method comprising administering an effective amount therefor of at least one compound according to claim 8 to the mammal.

* * * * *

UNITED STATES PATENT AND TRADEMARK OFFICE
CERTIFICATE OF CORRECTION

PATENT NO. : 8,653,101 B2
APPLICATION NO. : 13/218512
DATED : February 18, 2014
INVENTOR(S) : Kühnert et al.

It is certified that error appears in the above-identified patent and that said Letters Patent is hereby corrected as shown below:

In the specification

Column 1, line 46, "post" -- should read -- Dost --.

Column 5, line 19, "$C_{1-8}$" -- should read -- $C_{1-6}$ --.

Column 5, line 27, "$C_{1-8}$" -- should read -- $C_{1-6}$ --.

Column 24, line 51, "5-$C_{1-4}$" -- should read -- S-$C_{1-4}$ --.

Column 31, line 19, "phenylymethyl" -- should read -- phenyl)-methyl --.

Column 31, line 20, "phenylymethyl" -- should read -- phenyl)-methyl --.

Column 31, line 24, "phenylymethyl" -- should read -- phenyl)-methyl --.

Column 38, line 63, "$R^4 R^6$" -- should read -- $R^4 R^5, R^6$ --.

Column 39, line 30, "roniunnhexafluorophosphate" -- should read -- roniumhexafluorophosphate --.

Column 39, line 42, "Tetramethylethylendiannin" -- should read -- Tetramethylethylendiamin --.

In the claims

Column 54, line 16, "$R^{8c \text{ denotes a C}}_{1-4}$" -- should read -- $R^{8c}$ denotes a $C_{1-4}$ --.

Column 58, line 42, "$K^{30}$" -- should read -- $K^+$ --.

Signed and Sealed this
Nineteenth Day of July, 2016

Michelle K. Lee
*Director of the United States Patent and Trademark Office*